United States Patent
Nagamitsu et al.

(10) Patent No.: US 8,143,764 B2
(45) Date of Patent: Mar. 27, 2012

(54) FLAT STACKED-TYPE CONDUCTIVE POLYMER ACTUATOR

(75) Inventors: Sachio Nagamitsu, Kyoto (JP); Atsushi Ono, Kyoto (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/116,215

(22) Filed: May 26, 2011

(65) Prior Publication Data

US 2011/0227455 A1    Sep. 22, 2011

Related U.S. Application Data

(63) Continuation of application No. PCT/JP2010/005677, filed on Sep. 17, 2010.

(30) Foreign Application Priority Data

Sep. 24, 2009    (JP) .................................. 2009-218963

(51) Int. Cl.
*H01L 41/04* (2006.01)
*H01L 41/08* (2006.01)

(52) U.S. Cl. ........................................ 310/328; 310/800

(58) Field of Classification Search .................. 310/328, 310/800, 363
See application file for complete search history.

(56) References Cited

U.S. PATENT DOCUMENTS

| | | | | |
|---|---|---|---|---|
| 6,891,313 B1 * | 5/2005 | Henneken et al. | ............ | 310/328 |
| 7,576,475 B2 * | 8/2009 | Izumi et al. | .................. | 310/328 |
| 7,586,242 B2 * | 9/2009 | Yokoyama et al. | ........... | 310/365 |
| 7,692,361 B2 * | 4/2010 | Kato et al. | ..................... | 310/328 |
| 7,804,226 B2 * | 9/2010 | Asai | .............................. | 310/328 |
| 7,839,055 B2 * | 11/2010 | Nagamitsu et al. | ........... | 310/328 |
| 2008/0265709 A1 * | 10/2008 | Clausen et al. | ............... | 310/300 |

FOREIGN PATENT DOCUMENTS

| | | | |
|---|---|---|---|
| JP | 63-289975 | | 11/1988 |
| JP | 11-169393 | | 6/1999 |
| JP | 2006025507 A | * | 1/2006 |
| JP | 2006-125396 | | 5/2006 |
| JP | 3817259 | | 9/2006 |
| JP | 2007028749 A | * | 2/2007 |
| JP | 2008211916 A | * | 9/2008 |
| JP | 2008253016 A | * | 10/2008 |
| JP | 2009-044898 | | 2/2009 |
| JP | 4250536 | | 4/2009 |

(Continued)

OTHER PUBLICATIONS

International Search Report issued Dec. 28, 2010 in parent International (PCT) Application No. PCT/JP2010/005677.

*Primary Examiner* — Jaydi San Martin
(74) *Attorney, Agent, or Firm* — Wenderoth, Lind & Ponack, L.L.P.

(57) ABSTRACT

A first conductive polymer film, a plate-shaped first porous member, a second conductive polymer film, and a plate-shaped second porous member are stacked on one another, and the adjacent members are connected with each other on first end portions so as to form a zigzag pattern. The first and second porous members each have an ionic solution injected thereinto so as to function as an electrolyte retention layer, so that operations can be carried out with tensions being always maintained upon both of the expansion and the contraction, and rigidity and a driving force can be exerted in both of the contracting and expanding directions.

7 Claims, 26 Drawing Sheets

FOREIGN PATENT DOCUMENTS

| | | | |
|---|---|---|---|
| JP | 2010161870 A | * | 7/2010 |
| JP | 2010161894 A | * | 7/2010 |
| JP | 2010226949 A | * | 10/2010 |
| JP | 2010263750 A | * | 11/2010 |
| JP | 2011087460 A | * | 4/2011 |
| JP | 2011100861 A | * | 5/2011 |
| JP | 2011125092 A | * | 6/2011 |
| WO | 2005/114827 | | 12/2005 |

* cited by examiner

Fig. 10A - PRIOR ART

Fig. 10B - PRIOR ART
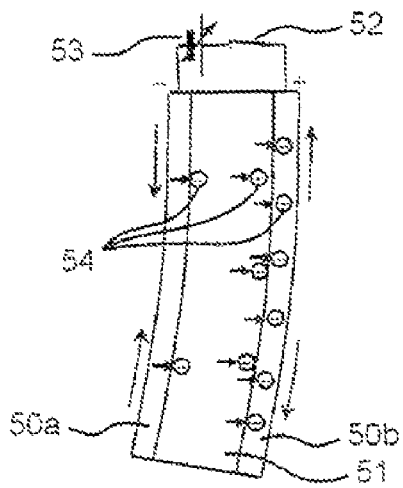
Fig. 10C - PRIOR ART
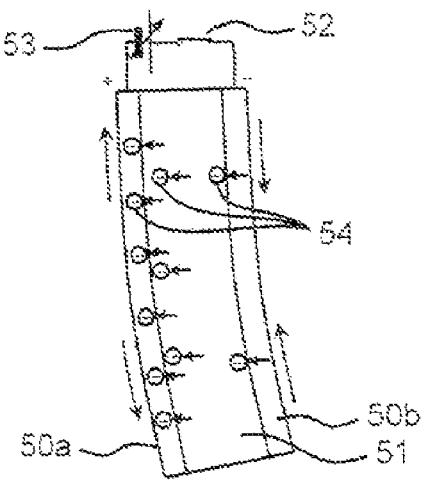
Fig. 11A - PRIOR ART
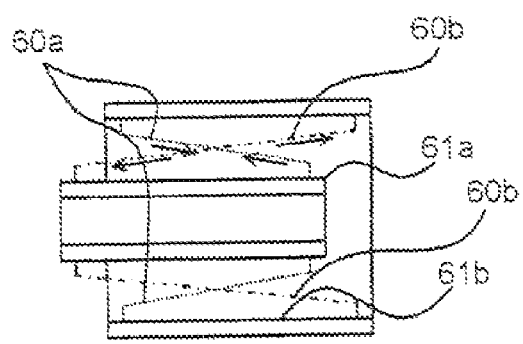

Fig. 11B - PRIOR ART
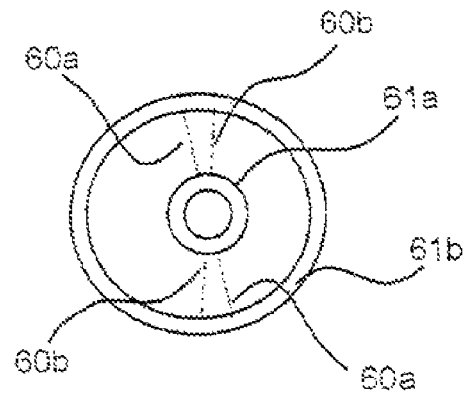
Fig. 11C - PRIOR ART
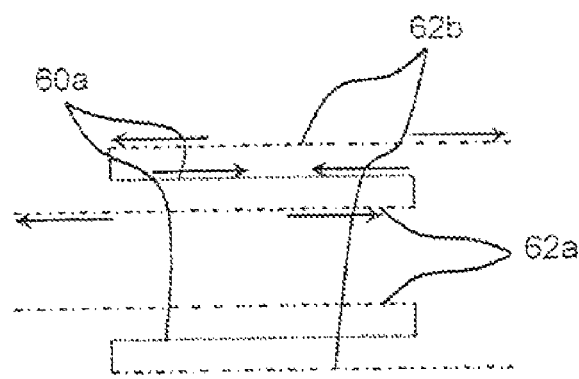
Fig. 12 - PRIOR ART
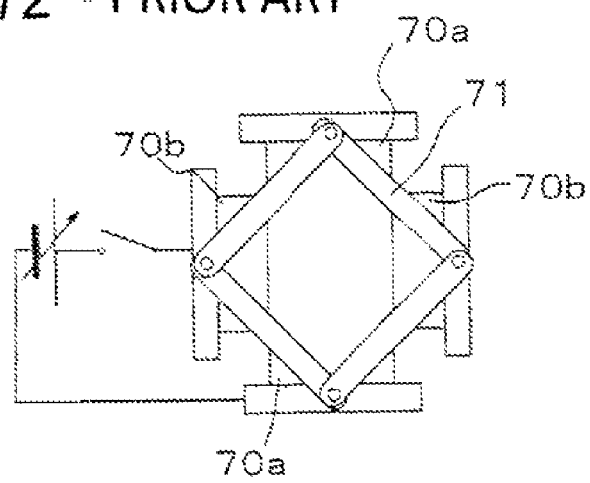

*Fig. 13A* - PRIOR ART
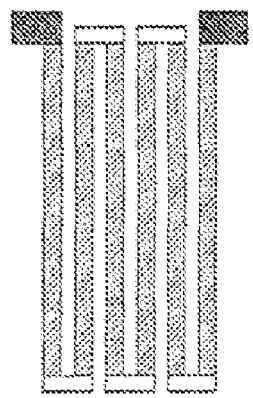
*Fig. 13B* - PRIOR ART
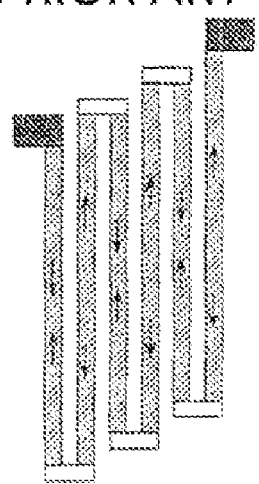
*Fig. 13C* - PRIOR ART
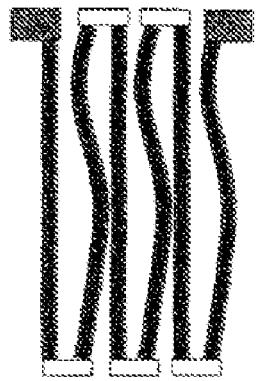

FLAT STACKED-TYPE CONDUCTIVE POLYMER ACTUATOR

This is a continuation application of International Application No. PCT/JP2010/005677, filed Sep. 17, 2010.

BACKGROUND OF THE INVENTION

The present invention relates to a flat stacked-type conductive polymer actuator that can expand a displacement by using stacked layers.

Due to the social background with the declining birthrate and the growing proportion of elderly people, there have been increasing needs to a machine working in the neighborhood of a person or in cooperation with a person, such as home-use robots. In this case, from the viewpoints of flexible movements to deal with complicated tasks and safety in case of crash with a person, there have been increasing expectations for an artificial muscle actuator which has a flexible characteristic like the muscle of the human being. For the artificial muscle actuator such as those using pneumatic pressure, various materials or control systems have been proposed. As one of these, in recent years, an actuator that uses a conductive polymer has been devised.

As one example of conventional actuators using conductive polymers, an actuator that utilizes a transformation of the bimorph type has been proposed (for example, see Patent Document 1: Japanese Unexamined Patent Publication No. 11-169393).

FIGS. 10A, 10B, and 10C show a conventional conductive polymer actuator described in Patent Document 1. FIG. 10A shows a structure in which a solid electrolyte molded body 51 is sandwiched between polyaniline film members 50a and 50b serving as conductive polymer films. Upon turning a switch 52 on, an electric potential difference set in a power supply 53 is applied between the polyaniline film members 50a and 50b so that, as shown in FIG. 10B, anions 54 are inserted into the one polyaniline film member 50b to be expanded, while anions 54 are separated from the other polyaniline film member 50a to be contracted, resulting in that a transformation of the bimorph type is generated. In a case where the electric potential difference is reversed, as shown in FIG. 10C, the transformation is generated in a direction reversed to that of FIG. 10B.

In this structure, the transformation is generated by a difference between the amounts of displacements of the two conductive polymer films 50a and 50b functioning as electrodes. In contrast, there has been known another structure in which, by preparing an electrolyte retention layer into a liquid or gel substance, the influences of the two electrodes are prevented from being exerted on each other so that only the displacement of one of the conductive polymers is taken out to carry out expansion/contraction as an actuator. In this case, the electrode that is not utilized for the transformation is not necessarily required to be a conductive polymer and a metal electrode is mainly used, on which a conductive polymer may be formed thereon.

Since such a conductive polymer actuator generates a stress equivalent to that of a muscle at a comparatively low voltage of 1.5 V to 3.0 V, it is expected to be put into practical use as an artificial muscle.

As the liquid or gel electrolyte retention layer, an ionic liquid, which is defined as a fused salt at room temperature, is used. The ionic liquid has drawn public attentions as a new functional liquid, and 1-butyl-3-methyl imidazolium or bis (trifluoromethylsulfonyl) imide has been known as the ionic liquid, in which charges of cations and anions are delocalized, so that only little Coulomb force is exerted between the two ions so as to be kept as a liquid at room temperature. Its vapor pressure is low to hardly cause vapor loss, and this liquid is nonflammable and usually superior in thermal and oxidization stability as well as has a high lubricating characteristic. This ionic liquid is applied to an insulating sheet or the ionic liquid itself is gelled so that the electrolyte retention layer is formed.

Moreover, since the conductive polymer is a film, a method has been proposed in which, by forming the conductive polymer film into a cylindrical shape, the conductive polymer film is prevented from being buckled so as to have rigidity (for example, see Patent Document 2: Japanese Unexamined Patent Publication No. 2006-125396). As shown in FIG. 11A, conductive polymer films 60a and 60b of two kinds for expansion and contraction are alternately disposed in a circumferential direction, and end portions of an inner cylindrical member 61a and an outer cylindrical member 61b are coupled to the films in a manner so as to be crossed with each other. Therefore, when one of the two kinds of conductive polymer films 60a and 60b is expanded, the other conductive polymer film holds a load so as to exert rigidity. FIG. 11B shows one example of a layout of the conductive polymer films 60a and 60b in the circumferential direction. Moreover, as shown in FIG. 11C, a method is also proposed in which, by preparing these cylindrical members as conductive polymer members 62a and 62b, the amounts of displacements are increased.

Moreover, as shown in FIG. 12, an actuator is proposed which exerts a driving force in an expanding direction and rigidity in a contracting direction without the necessity of applying a pre-load, in a structure in which conductive polymer films 70a and 70b are stacked in a crossed pattern, by connecting with use of a link mechanism 71 that mutually converts one displacement in the expanding direction to another displacement in the contracting direction (for example, see Patent Document 3: Japanese Patent No. 3817259).

Moreover, as shown in FIGS. 13A and 13B, a piezoelectric actuator is disclosed which can expand the amounts of displacements by both of expansion and contraction, with rigidity being maintained in the expanding and contraction directions (for example, see Patent Document 4: Japanese Unexamined Patent Publication No. 63-289975).

However, the actuators having the above-mentioned structures also have issues.

In the method of Patent Document 1, since the deformation of the bimorph type is utilized, it is difficult to freely change the displacement expanding or a stress expanding by further stacking the conductive polymer films. Although the length of the conductive polymer film can be changed so as to expand the displacement and the width of the conductive polymer film can be expanded so as to expand the stress, it is not possible to stack a plurality of conductive polymer films. This structure has difficulties in stacking the layers because electric short circuiting occurs due to the fact that the polarities of the adjacent conductive polymer films are reverse to each other and reductions in stress and displacement occur due to frictional resistance caused by the fact that the adjacent conductive polymer films are reversed to each other in expansion/contraction.

In the method of Patent Document 2, by forming the conductive polymer film into a cylindrical shape so as to provide rigidity, and by providing the structure in which, as shown in FIG. 11A, two kinds of films 60a and 60b that expand and contract in a circumferential direction of cylindrical members 61a and 61b are alternately aligned in the width direction, an issue arises in which effective insertion and separation of ions through the electrolyte retention layer are difficult, which is greatly different from the structure of Patent Document 1 shown in FIG. 10A in which the surfaces of the conductive polymer films face each other in the thickness direction. Even with an arrangement, unlike the arrangement shown in FIG. 11B, with a higher density in the circumferential direction, the efficiency of the ion mobility between the adjacent conductive polymer films would be lowered in comparison with the structure in which the surfaces of the polymer films face each other. Consequently, it is difficult to output a sufficient stress and displacement as an actuator. Moreover, in the structure shown in FIG. 11C, since no specific descriptions are made to a supporting member corresponding to the cylindrical member, buckling is generated in the conductive polymer films 62a and 62b, with a result that the actuator is not functional.

In the method of Patent Document 3, as shown in FIG. 12, the driving force in the expanding direction and rigidity in the contracting direction can be achieved without applying a pre-load in both of the expansion and contraction; however, there are disadvantages that directions in which the driving force can be taken out are dispersed into two directions crossing perpendicularly with each other, and that even when the number of the conductive polymer films 70a and 70b to be stacked is increased, the displacement cannot be increased.

In the method of Patent Document 4, as shown in FIGS. 13A and 13B, the amounts of displacements can be expanded in both of the expansion and contraction with rigidity in the expanding direction as well as in the contracting direction being maintained. However, this structure uses a solid member referred to as a piezoelectric body. If the structure uses a conductive polymer film, an issue of buckling is caused as shown in FIG. 13C. Since the conductive polymer film is not a solid material but is a film, a tension is exerted when pulled from the two ends, while in contrast, buckling might be caused when compressive stresses are applied from the two sides. In other words, in the structure in FIG. 13A, rigidity can be maintained in none of the expanding direction and the contracting direction.

In order to solve the conventional issues described above, an object of the present invention is to provide a flat stacked-type conductive polymer actuator that has rigidity and a driving force in both of the contracting direction and expanding direction, as well as can expand displacement by staking layers.

SUMMARY OF THE INVENTION

In order to achieve the above object, the present invention has the following structures.

In accordance with a first aspect of the present invention, there is provided a flat stacked-type conductive polymer actuator comprising:

a first conductive polymer film, a plate-shaped first porous member, a second conductive polymer film, and a plate-shaped second porous member, which are stacked on one another, wherein each of the first porous member and the second porous member has an ionic solution injected thereinto so as to function also as an electrolyte retention layer, a first end portion of the first porous member and a first end portion of the second conductive polymer film that are opposed to each other are connected to each other, a first end portion of the first conductive polymer film and a first end portion of the second porous member that are opposed to each other are connected to each other with a spacer being interposed therebetween, a second end portion of the first porous member and a second end portion of the first conductive polymer film that are opposed to each other are connected to each other, a second end portion of the second conductive polymer film and a second end portion of the second porous member that are opposed to each other are connected to each other, and by applying an electric potential difference between the first conductive polymer film and the second conductive polymer film, one of the first conductive polymer film and the second conductive polymer film is expanded or contracted and the other conductive polymer film is contracted or expanded by an oxidation-reduction reaction, so that a driving force is externally outputted by displacements of the first porous member and the second porous member.

In accordance with a fifth aspect of the present invention, there is provided a flat stacked-type conductive polymer actuator comprising:

an electrolyte retention layer;

a first conductive polymer film and a second conductive polymer film, having first end portions thereof being disposed to face each other and second end portions thereof being disposed to face each other, with the electrolyte retention layer being interposed therebetween;

a first fixing member that connects with each other a first end portion to be secured to an outer surface of the first end portion of the first conductive polymer film and a second end portion to be secured to an outer surface of the second end portion of the second conductive polymer film; and a second fixing member that connects with each other a first end portion to be secured to an outer surface of the first end portion of the second conductive polymer film and a second end portion to be secured to an outer surface of the second end portion of the first conductive polymer film, wherein by applying an electric potential difference between the first conductive polymer film and the second conductive polymer film, one of the first conductive polymer film and the second conductive polymer film is expanded or contracted and the other conductive polymer film is contracted or expanded by an oxidation-reduction reaction, so that a driving force is externally outputted by displacements of the first fixing member and the second fixing member.

With these structures, rigidity and a driving force are exerted in both of the contracting direction and the expanding direction of the displacement.

In accordance with the flat stacked-type conductive polymer actuator of the present invention, the rigidity and the driving force are exerted in both of the contracting direction and the expanding direction of the displacement.

BRIEF DESCRIPTION OF THE DRAWINGS

These and other aspects and features of the present invention will become clear from the following description taken in conjunction with the preferred embodiments thereof with reference to the accompanying drawings, in which:

FIG. 10A is a view that shows a structure, a voltage, and a direction of a displacement of a conventional conductive polymer actuator;

FIG. 10B is a view that shows a structure, a voltage, and a direction of a displacement of the conventional conductive polymer actuator;

FIG. 10C is a view that shows a structure, a voltage, and a direction of a displacement of the conventional conductive polymer actuator;

FIG. 11A is a view that shows a structure and a direction of a displacement of the conventional conductive polymer actuator;

FIG. 11B is a view that shows a structure and a direction of a displacement of the conventional conductive polymer actuator;

FIG. 11C is a view that shows a structure and a direction of a displacement of the conventional conductive polymer actuator;

FIG. 12 is a view that shows a structure of a conventional conductive polymer actuator;

FIG. 13A is a view that shows a structure of a conventional stacked-type actuator;

FIG. 13B is a view that shows a structure of a conventional stacked-type actuator; and FIG. 13C is a view that shows a structure of a conventional stacked-type actuator.

DESCRIPTION OF THE EMBODIMENTS

Figure 1A:
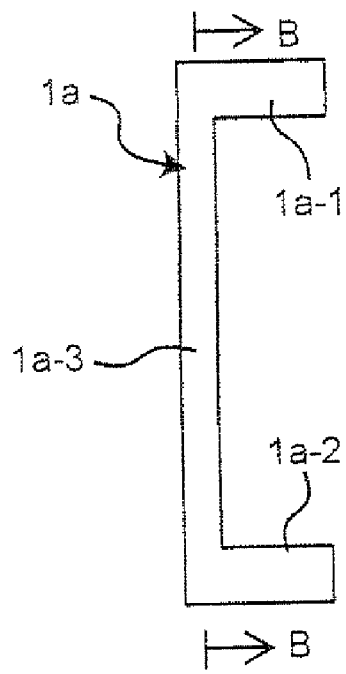
FIG. 1A is a front view that shows a structure of a first fixing member of a flat stacked-type conductive polymer actuator in accordance with a first embodiment of the present invention.

Before the description of the present invention proceeds, it is to be noted that like parts are designated by like reference numerals throughout the accompanying drawings.

Prior to the detailed description of embodiments of the present invention based upon the drawings, various aspects for the present invention will be explained.

In accordance with a first aspect of the present invention, there is provided a flat stacked-type conductive polymer actuator comprising:

a first conductive polymer film, a plate-shaped first porous member, a second conductive polymer film, and a plate-shaped second porous member, which are stacked on one another, wherein each of the first porous member and the second porous member has an ionic solution injected thereinto so as to function also as an electrolyte retention layer, a first end portion of the first porous member and a first end portion of the second conductive polymer film that are opposed to each other are connected to each other, a first end portion of the first conductive polymer film and a first end portion of the second porous member that are opposed to each other are connected to each other with a spacer being interposed therebetween, a second end portion of the first porous member and a second end portion of the first conductive polymer film that are opposed to each other are connected to each other, a second end portion of the second conductive polymer film and a second end portion of the second porous member that are opposed to each other are connected to each other, and by applying an electric potential difference between the first conductive polymer film and the second conductive polymer film, one of the first conductive polymer film and the second conductive polymer film is expanded or contracted and the other conductive polymer film is contracted or expanded by an oxidation-reduction reaction, so that a driving force is externally outputted by displacements of the first porous member and the second porous member.

In accordance with a second aspect of the present invention, there is provided the flat stacked-type conductive polymer actuator according to the first aspect, wherein the first porous member and the second conductive polymer film have a same length, the first conductive polymer film and the second porous member have a same length, and the length of the first porous member and the second conductive polymer film is smaller than the length of the first conductive polymer film and the second porous member.

In accordance with a third aspect of the present invention, there is provided the flat stacked-type conductive polymer actuator according to the first or second aspect, wherein at least a part of a peripheral portion of the porous member contains a curing agent.

In accordance with a fourth aspect of the present invention, there is provided a collective flat stacked-type conductive polymer actuator comprising a plurality of flat stacked-type conductive polymer actuators according to claim 1 or 2, wherein the first porous member and the second porous member of the adjacent actuators are connected with each other by using a link member.

In accordance with a fifth aspect of the present invention, there is provided a flat stacked-type conductive polymer actuator comprising:

an electrolyte retention layer;

a first conductive polymer film and a second conductive polymer film, having first end portions thereof being disposed to face each other and second end portions thereof being disposed to face each other, with the electrolyte retention layer being interposed therebetween;

a first fixing member that connects with each other a first end portion to be secured to an outer surface of the first end portion of the first conductive polymer film and a second end portion to be secured to an outer surface of the second end portion of the second conductive polymer film; and a second fixing member that connects with each other a first end portion to be secured to an outer surface of the first end portion of the second conductive polymer film and a second end portion to be secured to an outer surface of the second end portion of the first conductive polymer film, wherein by applying an electric potential difference between the first conductive polymer film and the second conductive polymer film, one of the first conductive polymer film and the second conductive polymer film is expanded or contracted and the other conductive polymer film is contracted or expanded by an oxidation-reduction reaction, so that a driving force is externally outputted by displacements of the first fixing member and the second fixing member.

In accordance with a sixth aspect of the present invention, there is provided the flat stacked-type conductive polymer actuator according to fifth aspect, wherein the first conductive polymer film and the second conductive polymer film have a same length.

In accordance with a seventh aspect of the present invention, there is provided a collective flat stacked-type conductive polymer actuator comprising a plurality of flat stacked-type conductive polymer actuators according to the fifth or sixth aspect, wherein in each of the actuators, by an oxidation-reduction reaction caused by applying an electric potential difference between the conductive polymer films that are connected to each other with the electrolyte retention layer interposed therebetween, one of the adjacent conductive polymer films is expanded or contracted and the other conductive polymer film is contracted or expanded, an adhesive agent is provided to connect the second fixing member of one of the least two or more adjacent flat conductive polymer actuators to the first fixing member of the other actuator, and by connecting the actuators with the adhesive agent, the displacements are added and increased.

First Embodiment

FIGS. 1A to 1G are views that show a structure of a flat stacked-type conductive polymer actuator 14 in a first embodiment of the present invention.

Figure 1B:
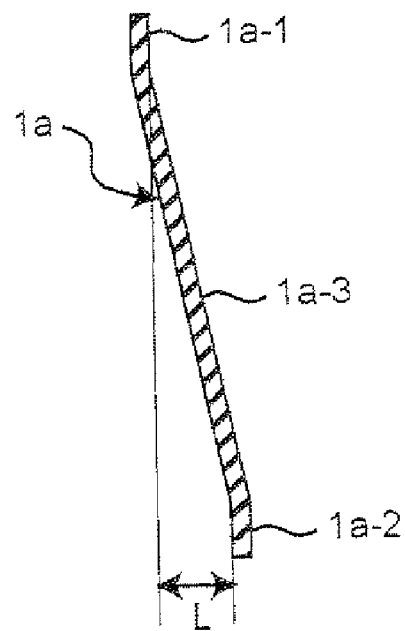
FIG. 1B is a B-B line cross-sectional side view of FIG. 1A.
Figure 1C:
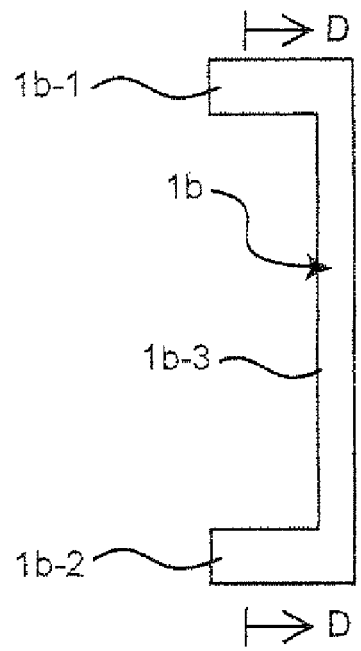
FIG. 1C is a front view that shows a structure of a second fixing member of the flat stacked-type conductive polymer actuator in accordance with the first embodiment of the present invention.
Figure 1D:
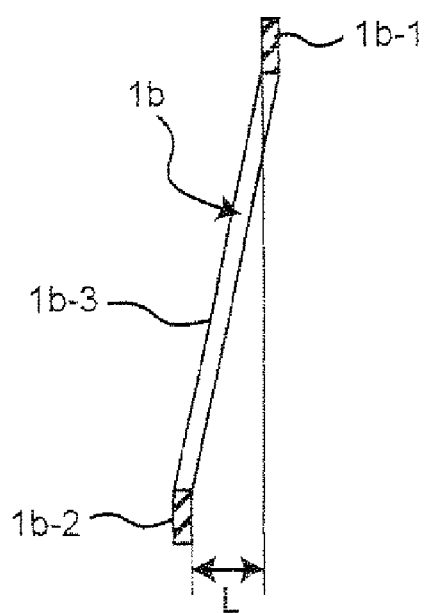
FIG. 1D is a D-D line cross-sectional side view of FIG. 1C.

In FIGS. 1A to 1G, the flat stacked-type conductive polymer actuator 14 is configured by a first fixing member 1a provided as a plate member having a substantially C-letter shape as shown in FIGS. 1A and 1B, a second fixing member 1b provided as a plate member having a substantially C-letter shape as shown in FIGS. 1C and 1D, a first conductive polymer film 2a, a second conductive polymer film 2b, and an electrolyte retention layer 3.

Each of the first conductive polymer film 2a and the second conductive polymer film 2b is a flexible film member having a quadrangular shape, such as a rectangular shape, made of a conductive polymer that is deformed to expand and contract in response to an oxidation-reduction reaction.

The thickness of each of the conductive polymer films 2a, 2b is preferably set in a range of from 5 μm to 30 μm. Although greatly depending on the material thereof, the thickness of each of the conductive polymer film 2a, 2b thinner than 5 μm is weak in strength, while the thickness greater than 30 μm is not preferable because it is difficult to allow incoming and outgoing ions to reach the inside of the film to reduce a generated displacement and also to cause a reduction in motion speed. In one actual example of the first embodiment, there are used the conductive polymer films 2a, 2b, each having 15 μm in thickness, 50 mm in length, and 10 mm in width. Moreover, in the actual example, the thickness of the electrolyte retention layer 3 is 40 μm, and as each of the first fixing member 1a and the second fixing member 1b, a Teflon (registered trademark) sheet having a thickness of 100 μm is used. Moreover, as will be described later, since an extra margin of about several tens μm is required, the structure in FIG. 1 has a thickness of 290 μm in the actual example.

Figure 1E:
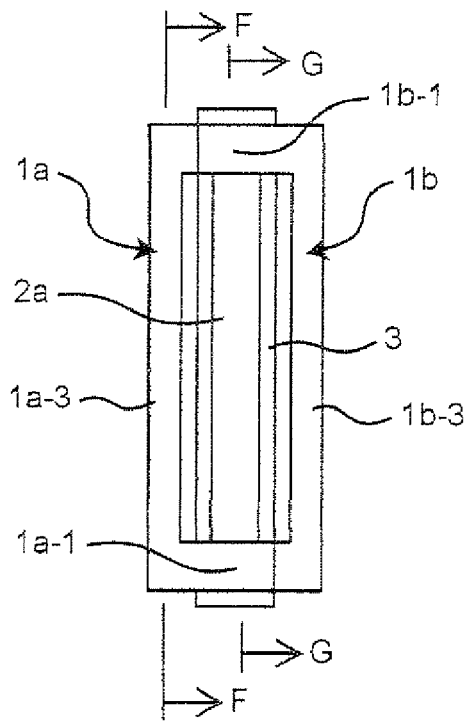
FIG. 1E is a front view that shows a structure of the flat stacked-type conductive polymer actuator in accordance with the first embodiment of the present invention.
Figure 1F:
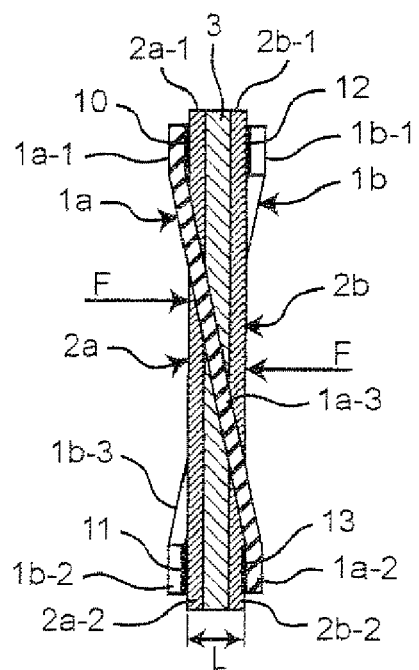
FIG. 1F is an F-F line cross-sectional side view of FIG. 1E.
Figure 1G:
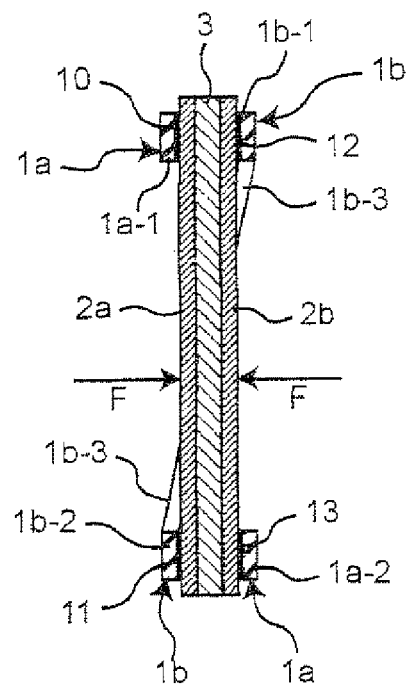
FIG. 1G is a G-G line cross-sectional side view of FIG. 1E.

In FIGS. 1E to 1G, the first conductive polymer film 2a and the second conductive polymer film 2b are disposed so as to face each other with the electrolyte retention layer 3 interposed therebetween. In this case, as shown in FIGS. 1E to 1G, on the upper portion of each of FIGS. 1E to 1G, a first end portion 2a-1 of the first conductive polymer film 2a and a first end portion 2b-1 of the second conductive polymer film 2b face each other with the electrolyte retention layer 3 interposed therebetween. On the lower portion of each of FIGS. 1E to 1G, a second end portion 2a-2 of the first conductive polymer film 2a and a second end portion 2b-2 of the second conductive polymer film 2b face each other with the electrolyte retention layer 3 interposed therebetween.

As shown in FIGS. 1A and 1B, the first fixing member 1a is provided as a plate member having a substantially C-letter shape, and has a first end portion 1a-1 having a laterally elongated quadrangular shape on the upper end, a second end portion 1a-2 having a laterally elongated quadrangular shape on the lower end, and a coupling portion 1a-3 having an longitudinally elongated quadrangular shape and coupling the first end portion 1a-1 to the second end portion 1a-2. The first fixing member 1a does not have a plane structure that includes the first end portion 1a-1, the second end portion 1a-2, and the coupling portion 1a-3 on an identical plane, but the first end portion 1a-1 and the second end portion 1a-2 are located in planes different from each other, with the first end portion 1a-1 and the second end portion 1a-2 being coupled to each other by the coupling portion 1a-3. More specifically, the first fixing member 1a is three-dimensionally configured such that the second end portion 1a-2 is positioned on a plane different in the thickness direction of the first fixing member 1a from the plane including the first end portion 1a-1, by a dimension L (for example, in a case of being larger by $\Delta T$, $L=T+\Delta T$) that is slightly larger than a total dimension T ($=T_{2a}+T_3+T_{2b}$) of at least a thickness $T_{2a}$ of the first conductive polymer film 2a, a thickness $T_3$ of the electrolyte retention layer 3, and a thickness $T_{2b}$ of the second conductive polymer film 2b, with the first end portion 1a-1 and the second end portion 1a-2 being coupled to each other by the coupling portion 1a-3. For example, $\Delta T$ is preferably set to about several tens μm, as will be described later.

Moreover, in FIGS. 1E to 1G, the first end portion 1a-1 of the first fixing member 1a on the upper end side is secured to an outer surface of the first end portion 2a-1 of the first conductive polymer film 2a by using an adhesive agent 10. The second end portion 1a-2 of the first fixing member 1a on the lower end side is secured to an outer surface of the second end portion 2b-2 of the second conductive polymer film 2b in a manner so as to bridge over a side portion of a stacked body including the first conductive polymer film 2a, the electrolyte retention layer 3, and the second conductive polymer film 2b, by using an adhesive agent 13.

In the same manner, as shown in FIGS. 1C and 1D, the second fixing member 1b is provided as a plate member having a substantially C-letter shape directed in a direction reversed to the direction of the first fixing member 1a, and has a first end portion 1b-1 having a laterally elongated quadrangular shape on the upper end, a second end portion 1b-2 having a laterally elongated quadrangular shape on the lower end, and a coupling portion 1b-3 having an longitudinally elongated quadrangular shape and coupling the first end portion 1b-1 to the second end portion 1b-2. The second fixing member 1b does not have a plane structure that includes the first end portion 1b-1, the second end portion 1b-2, and the coupling portion 1b-3 on an identical plane, but the first end portion 1b-1 and the second end portion 1b-2 are located in planes different from each other, with the first end portion 1b-1 and the second end portion 1b-2 being coupled to each other by the coupling portion 1b-3. More specifically, the second fixing member 1b is three-dimensionally configured such that the second end portion 1b-2 is positioned on a plane different in the thickness direction of the second fixing member 1b from the plane including the first end portion 1b-1, by the dimension L (for example, in a case of being larger by $\Delta T$, $L=T+\Delta T$) that is slightly larger than the total dimension T ($=T_{2a}+T_3+T_{2b}$) of at least the thickness $T_{2a}$ of the first conductive polymer film 2a, the thickness $T_3$ of the electrolyte retention layer 3, and the thickness $T_{2b}$ of the second conductive polymer film 2b, with the first end portion 1b-1 and the second end portion 1b-2 being coupled to each other by the coupling portion 1b-3. For example, $\Delta T$ is preferably set to about several tens μm, as will be described later.

Moreover, in FIGS. 1E to 1G, the first end portion 1b-1 of the second fixing member 1b on the upper end side is secured to the outer surface of the first end portion 2b-1 of the second conductive polymer film 2b by using an adhesive agent 12. The second end portion 1b-2 of the second fixing member 1b on the lower end side is secured to the outer surface of the second end portion 2a-2 of the first conductive polymer film 2a in a manner so as to bridge over the side portion of the stacked body including the first conductive polymer film 2a, the electrolyte retention layer 3, and the second conductive polymer film 2b, by using an adhesive agent 11.

As described above, the first fixing member 1a and the second fixing member 1b are respectively allowed to maintain the distances between the inner surfaces (surfaces fixed with the conductive polymer films) of the first end portions 1a-1 and 1b-1 and the inner surfaces (surfaces fixed with the conductive polymer films) of the second end portions 1a-2 and 1b-2, each by the dimension L (for example, in a case of being larger by $\Delta T$, $L=T+\Delta T$) that is slightly larger than the total dimension T ($=T_{2a}+T_3+T_{2b}$) of at least the thickness $T_{2a}$ of the first conductive polymer film 2a, the thickness $T_3$ of the electrolyte retention layer 3, and the thickness $T_{2b}$ of the second conductive polymer film 2b. It is because, when the distance is equal to or less than the total dimension T, the first conductive polymer film 2a, the second conductive polymer film 2b, and the electrolyte retention layer 3 are made in contact with one another by a pressure being applied to the first conductive polymer film 2a, the second conductive polymer film 2b, and the electrolyte retention layer 3 from the first fixing member 1a and the second fixing member 1b, with a result that resistance exerted upon allowing the first conductive polymer film 2a and the second conductive polymer film 2b to respectively expand and contract rapidly increases to cause a reduction in each of the amounts of displacements of the first conductive polymer film 2a and the second conductive polymer film 2b. In order to prevent this reduction, an arrangement is desirably made so that contact of a degree such as providing a minute gap of about several tens μm in total is provided between the first conductive polymer film 2a and the electrolyte retention layer 3 as well as between the second conductive polymer film 2b and the electrolyte retention layer 3.

In this case, the electrolyte retention layer 3 is prepared in most cases by impregnating a separator with an ionic liquid so as to prevent electric short circuiting between the adjacent first conductive polymer film 2a and the second conductive polymer film 2b.

Figure 2A:
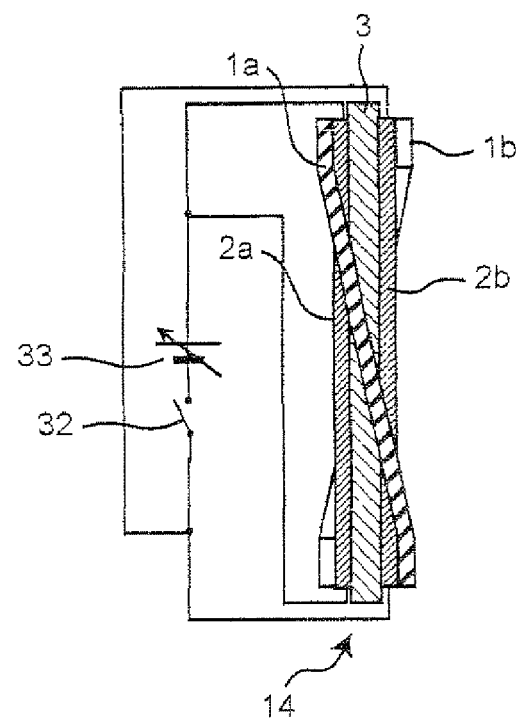
FIG. 2A is a view for describing a voltage and a direction of a displacement of the flat stacked-type conductive polymer actuator in accordance with the first embodiment of the present invention.

FIG. 2A shows a structure in which a switch 32 and a variable DC power supply 33 are installed between one end (for example, the upper end) and the other end (for example, the lower end) of the first conductive polymer film 2a, as well as between one end (for example, the upper end) and the other end (for example, the lower end) of the second conductive polymer film 2b so that the actuator 14 can be driven, that is, an electric potential difference can be applied between the first conductive polymer film 2a and the second conductive polymer film 2b. Prior to the driving of the actuator 14, the first conductive polymer film 2a and the second conductive polymer film 2b are maintained in a substantially expanded state respectively, by rigidity of each of the first fixing member 1a and the second fixing member 1b. For this reason, the first conductive polymer film 2a and second conductive polymer film 2b are maintained in a constant state by the tensions of the first conductive polymer film 2a and the second conductive polymer film 2b, without being buckled, even upon receipt of an external force F (see FIG. 1G) applied in a direction (in the thickness direction of each of the first conductive polymer film 2a and the second conductive polymer film 2b) perpendicular to the longitudinal direction of the first conductive polymer film 2a and the second conductive polymer film 2b.

Figure 2B:
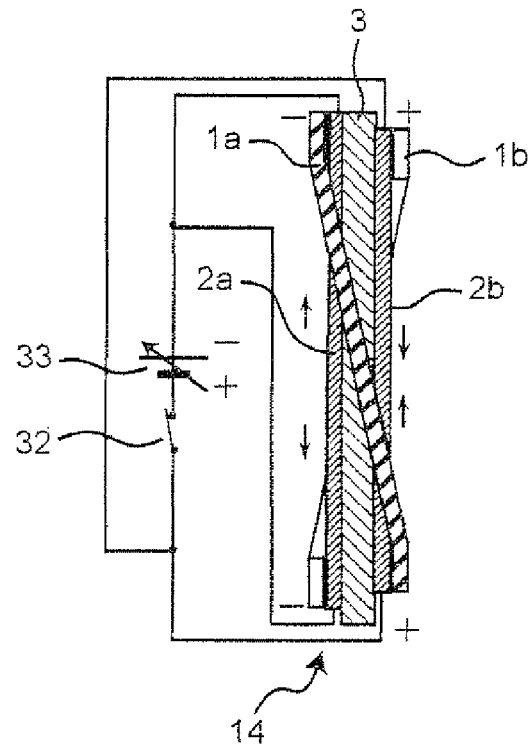
FIG. 2B is a view for describing a voltage and a direction of a displacement of the flat stacked-type conductive polymer actuator in accordance with the first embodiment of the present invention.
Figure 2C:
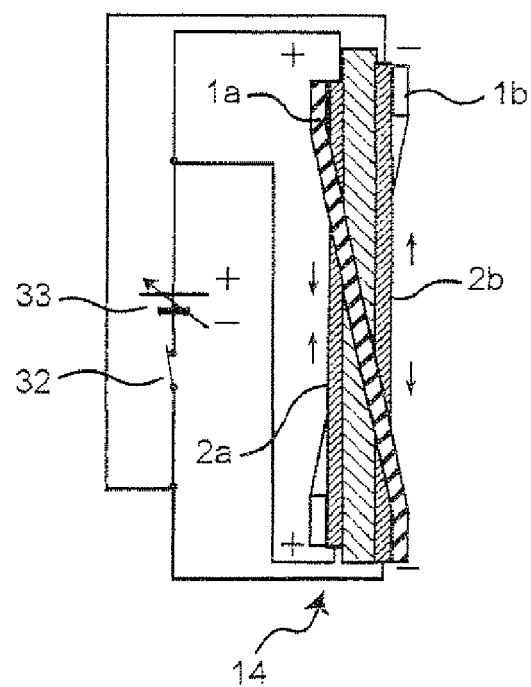
FIG. 2C is a view for describing a voltage and a direction of a displacement of the flat stacked-type conductive polymer actuator in accordance with the first embodiment of the present invention.

In this structure, as shown in FIGS. 2B and 2C, by turning the switch 32 on, one of the first conductive polymer film 2a and the second conductive polymer film 2b is expanded or contracted, while the other conductive polymer film is contracted or expanded, by an oxidation-reduction reaction. As a result, by the displacements of the first fixing member 1a and the second fixing member 1b, a driving force of the actuator 14 can be externally outputted. For example, in FIG. 2B, in comparison with the state shown in FIG. 2A, the first conductive polymer film 2a is expanded along the longitudinal direction thereof and the second conductive polymer film 2b is contracted along the longitudinal direction thereof, so that the first fixing member 1a is raised while the second fixing member 1b is lowered. In contrast, in FIG. 2C, in comparison with the state shown in FIG. 2A, the first conductive polymer film 2a is contracted along the longitudinal direction thereof and the second conductive polymer film 2b is expanded along the longitudinal direction thereof, so that the first fixing member 1a is lowered while the second fixing member 1b is raised. Therefore, the driving force can be externally outputted from the actuator 14 by the displacements of the first fixing member 1a and the second fixing member 1b each raised or lowered.

Each of the first fixing member 1a and the second fixing member 1b is preferably made of an insulating material, and a PEEK material or Teflon (registered trademark) (polytetrafluoroethylene) is preferably used. In a case of a structure including a plurality of actuators disposed adjacent to one another as in a second embodiment to be described later, Teflon (registered trademark), which has low frictional resistance upon contact in motion, is most preferably used. Moreover, acrylic materials or the like having a property to be dissolved in an ionic solution as will be described later are inappropriate as the material for the first fixing member 1a and the second fixing member 1b.

Moreover, since the first conductive polymer film 2a and the second conductive polymer film 2b have the large amounts of displacements by expansion and contraction, polypyrrole is used in most cases; however, since polypyrrole is oxidized by oxygen in the air in the long run with a result that the conductive performance might deteriorate, thiophene-based materials, such as PEDOT (polyethylene dioxythiophene), are more preferably used rather than polypyrrole. In the case of the thiophene-based material, there are two film-forming processes, namely, casting and electrolytic polymerization. In the former, the film formation is carried out by using PEDOT/PSS (polymer of styrene sulfonic acid) and drying from the water-soluble state, while in the case of the latter, the film formation is carried out by synthesizing in an electrochemical process in a solution containing EDOT (3,4-ethylene dioxythiophene) molecules.

As the adhesive agents 10, 11, 12, and 13, epoxy-based adhesive agents that have been widely used can be applied in most cases.

Furthermore, the separator for the electrolyte retention layer 3 can adopt cellulose as the base, which is used in an electric double-layered capacitor or the like. As the ionic solution for the electrolyte retention layer 3, BMIM.TFSI, that is, 1-butyl-3-methylimidazolium bis(trifluoromethylsulfonyl)imide, is proposed. In order to improve the expansion/contraction performance in polypyrrole or PEDOT (polyethylene dioxythiophene), EMI.TFSI, that is, 1-ethyl-3-methyl imidazolium bis(trifluoromethylsulfonyl)imide can be used.

Moreover, in the variable DC power supply 33, a voltage of about ±1.5 V may be applicable in association with an electric potential window of the ionic solution of the electrolyte retention layer 3. This voltage needs to be varied depending on the types of the conductive polymer films or the ionic solution to be used, by taking the durability into consideration.

Furthermore, the above-mentioned materials are only the examples, and the present invention is not intended to be limited to these materials.

In accordance with the structure of the first embodiment, since the two ends of each of the first conductive polymer film 2a and the second conductive polymer film 2b are secured by the first fixing member 1a and the second fixing member 1b, the actuator can be operated with the tension being always maintained in both of expansion and contraction. Therefore, upon the displacements of the first fixing member 1a and the second fixing member 1b, rigidity and a driving force can be exerted in both of the contracting direction and the expanding direction.

In the first embodiment, the first conductive polymer film 2a and the second conductive polymer film 2b are provided to have the same length; alternatively, by forming the first conductive polymer film 2a and the second conductive polymer film 2b in combinations with different thicknesses and materials, the displacements of expansions and contractions of the first conductive polymer film 2a and the second conductive polymer film 2b caused by an oxidation-reduction reaction may be made to be equal to each other.

In the first embodiment, when the first fixing member 1a and the second fixing member 1b are connected with the first conductive polymer film 2a and the second conductive polymer film 2b, the adhesive agents 10, 11, 12, and 13 are used; alternatively, without additionally using the adhesive agents, upon curing in the casting process during the formation of each of the first conductive polymer film 2a and the second conductive polymer film 2b, the first conductive polymer film 2a and the second conductive polymer film 2b may be connected with the first fixing member 1a and the second fixing member 1b, or upon deposition in the electrochemical polymerization process with the first conductive polymer film 2a and the second conductive polymer film 2b, these members may be connected with each other. Further alternatively, by installing an additional member, a mechanical connecting method may be carried out in which the first conductive polymer film 2a, the second conductive polymer film 2b, the first fixing member 1a, and the second fixing member 1b are sandwiched so as to be connected to one another.

As having been described earlier, as the electrolyte retention layer 3, the separator impregnated with the ionic solution is used so as to prevent electric short circuiting between the adjacent first conductive polymer film 2a and the second conductive polymer film 2b; alternatively, there are another methods in which beads are mixed and electric short circuiting is prevented with the lubricating property being maintained, or in which a gelled ionic solution is used and the separator is not provided. Upon carrying out the gelling process, for example, a method is proposed in which PDVF (polyvinylidene fluoride) is mixed therein.

Second Embodiment

FIG. 3 is a view that shows a structure of a flat stacked-type conductive polymer actuator 16 in accordance with a second embodiment of the present invention. In FIG. 3, the components same as those in FIGS. 1A to 1G and FIGS. 2A to 2C are indicated by the same reference symbols, and the description thereof will not be repeatedly provided.

Figure 3A:
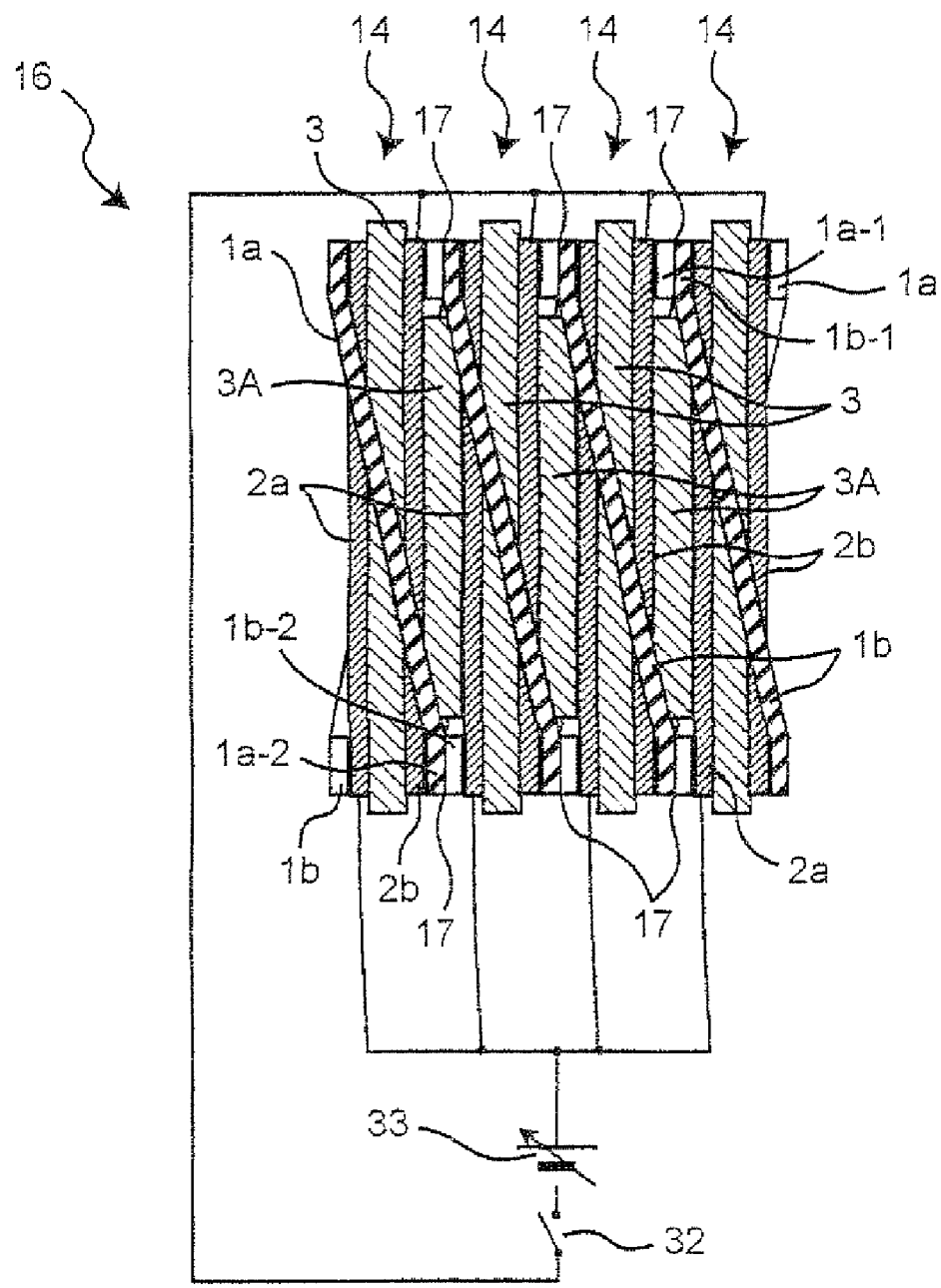
FIG. 3A is a view for describing a stacked structure, a voltage, and a displacement of a flat stacked-type conductive polymer actuator in accordance with a second embodiment of the present invention.

In FIG. 3A, the flat stacked-type conductive polymer actuator 16 of the second embodiment has the following structure.

More specifically, by using the flat conductive polymer actuator 14 in accordance with the first embodiment as one structural unit, a plurality of actuators 14 are disposed in parallel with one another so that the actuator 16 is formed. Moreover, the respective actuators 14 are connected to one after another, with coupling electrolyte retention layers 3A that each have the same structure as that of the electrolyte retention layer 3 being interposed therebetween. Furthermore, out of at least two or more adjacent flat conductive polymer actuators 14, the outer surface of the first end portion 1b-1 of the second fixing member 1b of one flat conductive polymer actuator 14 is connected to the outer surface of the first end portion 1a-1 of the first fixing member 1a of another flat conductive polymer actuator 14 by using an adhesive agent 17. The outer surface of the second end portion 1b-2 of the second fixing member 1b of the one flat conductive polymer actuator 14 is connected to the outer surface of the second end portion 1a-2 of the first fixing member 1a of the other flat conductive polymer actuator 14 by using the adhesive agent 17. The adhesive agent 17 may be, for example, the same as one of the adhesive agents 10 to 13.

FIG. 3A shows a structure in which the switch 32 and the variable DC power supply 33 are installed between one end (for example, the upper end) of the second conductive polymer film 2b and another end (for example, the lower end) of the first conductive polymer film 2a of each of the flat conductive polymer actuators 14, so that the respective actuators 14, that is, the actuator 16, can be driven, in other words, an electric potential difference can be applied between the first conductive polymer film 2a and the second conductive polymer film 2b.

Figure 3B:
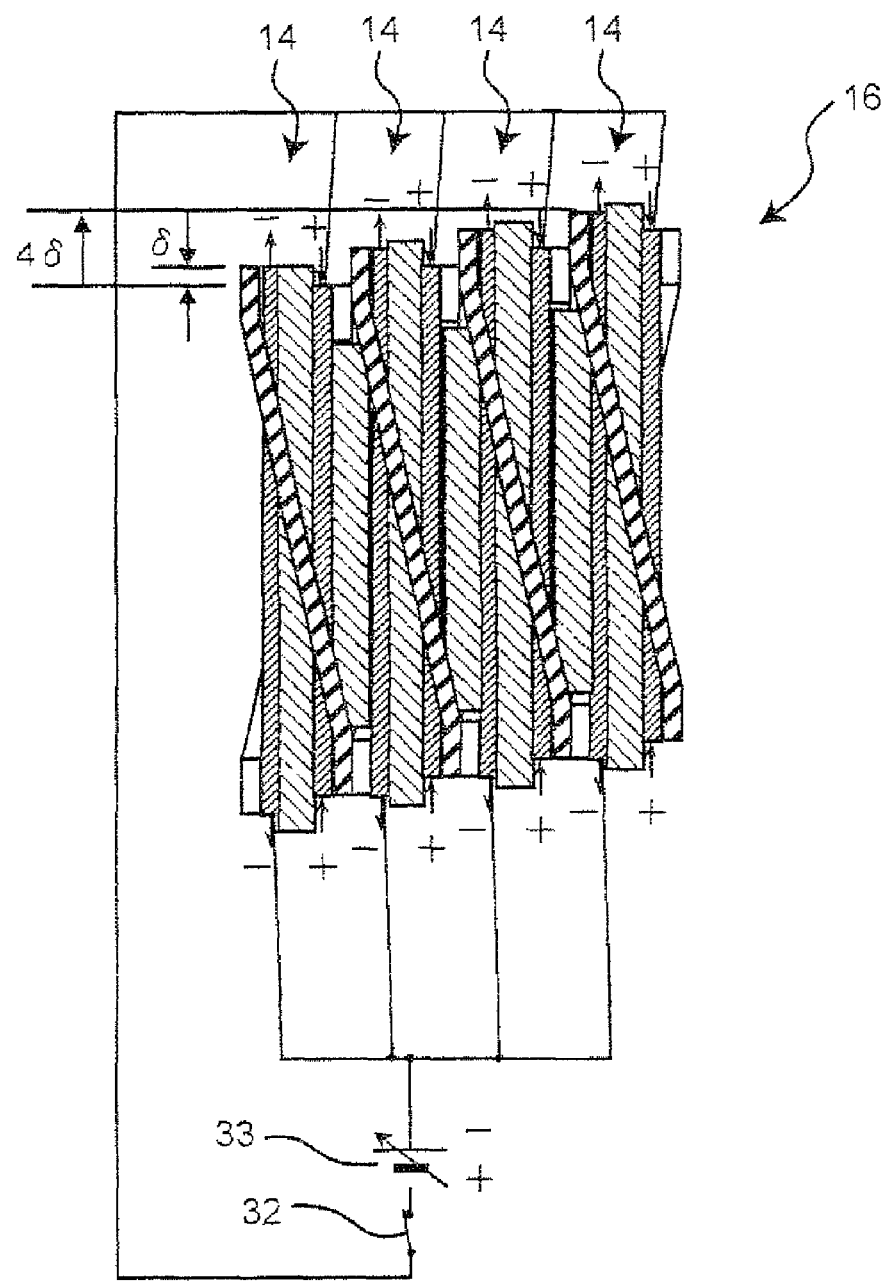
FIG. 3B is a view for describing a stacked structure, a voltage, and a displacement of the flat stacked-type conductive polymer actuator in accordance with the second embodiment of the present invention.
Figure 3C:
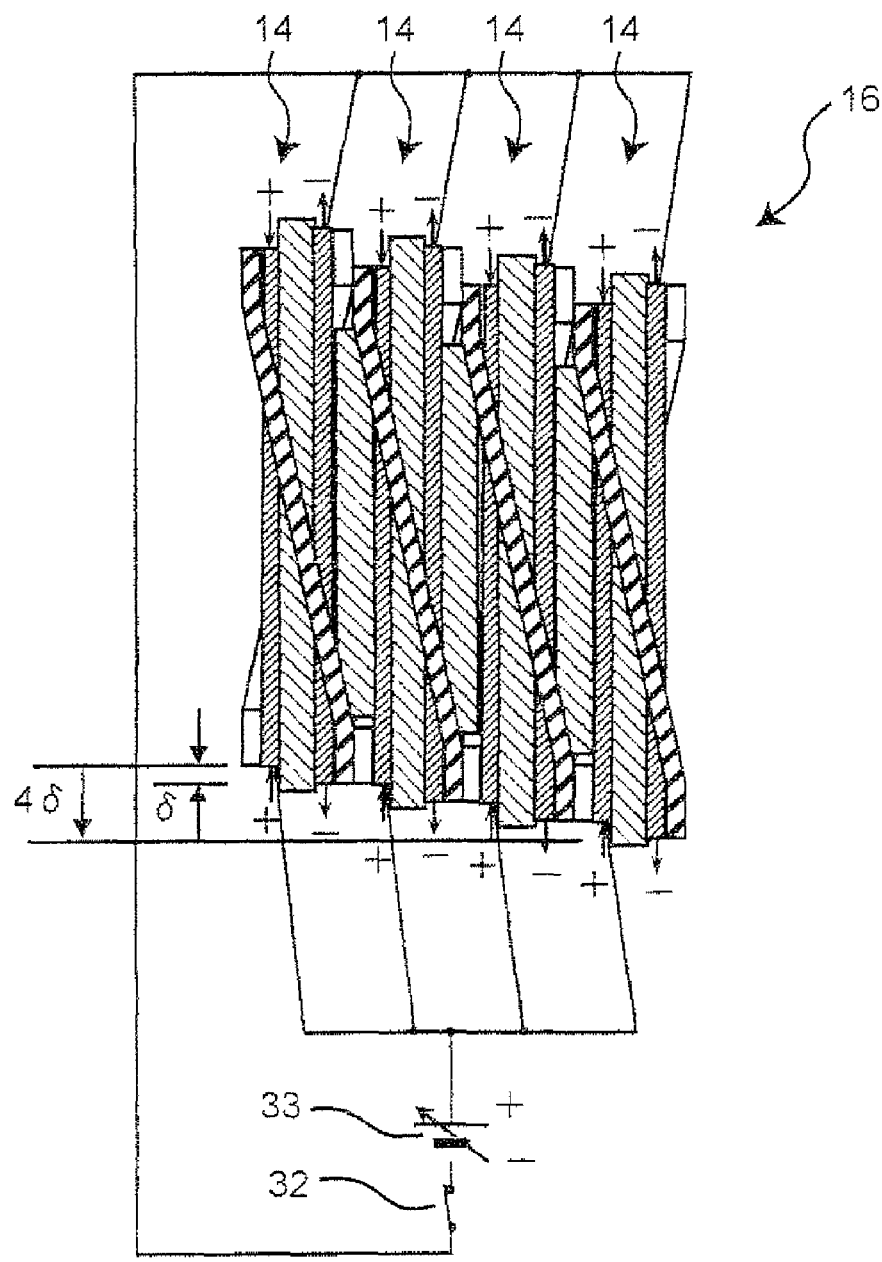
FIG. 3C is a view for describing a stacked structure, a voltage, and a displacement of the flat stacked-type conductive polymer actuator in accordance with the second embodiment of the present invention.

In this structure, as shown in FIGS. 3B and 3C, by turning the switch 32 on, one of the first conductive polymer film 2a and the second conductive polymer film 2b is expanded or contracted, while the other conductive polymer film is contracted or expanded, by an oxidation-reduction reaction. As a result, by the displacements of the first fixing member 1a and the second fixing member 1b, a driving force of the actuator 16 can be externally outputted as in the first embodiment. However, out of the adjacent two actuators 14 that are newly positioned next to each other and are connected by the adhesive agent 17 to face each other with the electrolyte retention layer 3A being interposed therebetween, since an oxidation-reduction reaction is generated by an electric potential difference also between the second conductive polymer film 2b of one of the actuators 14 and the first conductive polymer film 2a of the other actuator 14, the amounts of expansion/contraction displacements between the first conductive polymer film 2a and the second conductive polymer film 2b can be increased. In this case, supposing that the displacement between the paired first conductive polymer film 2a and second conductive polymer film 2b of one actuator 14 is δ, the four pairs of actuators 14 are respectively connected to one another by using the adhesive agent 17, so that a displacement increased to δ×4=4δ can be obtained.

Figure 4A:
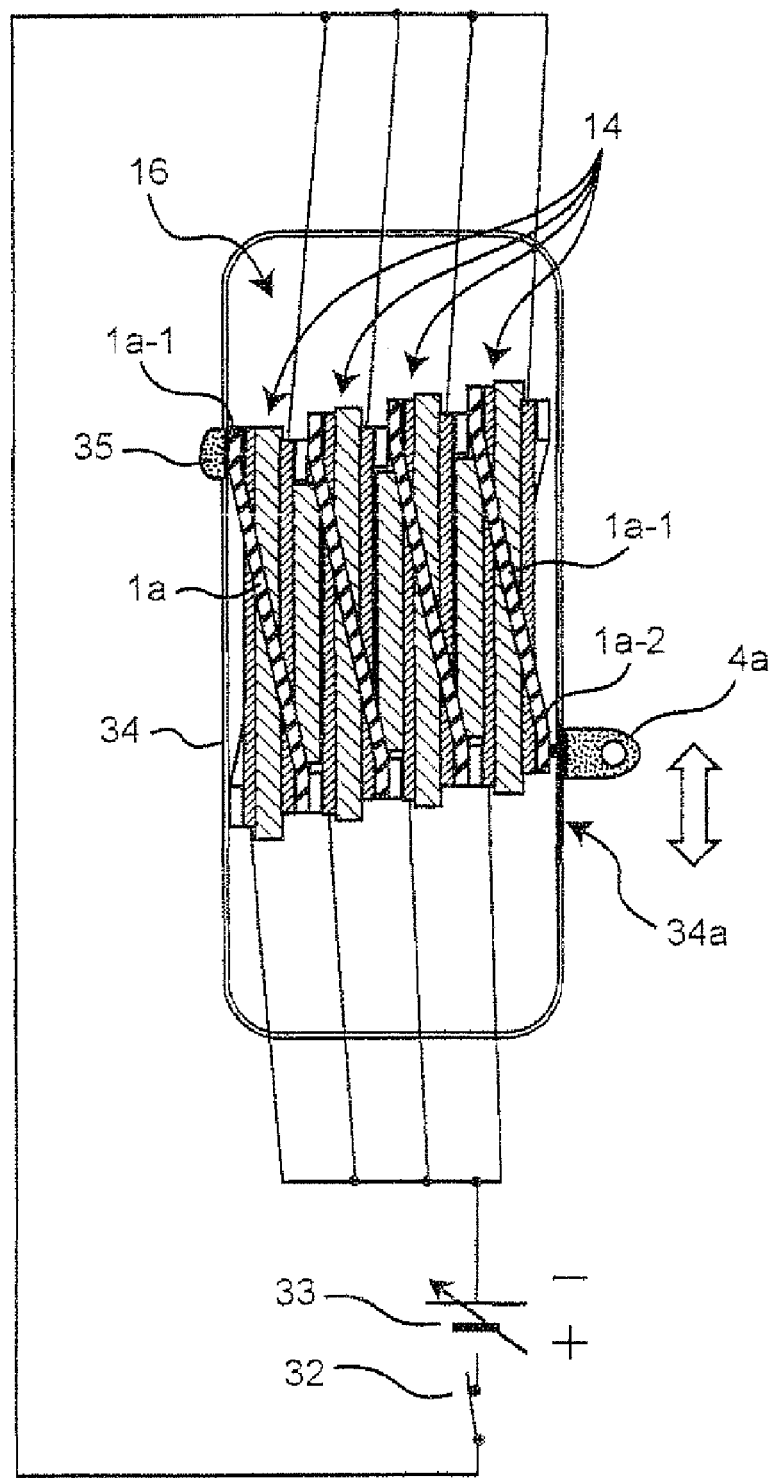
FIG. 4A is a view that shows a structure for use in externally outputting a driving force of the flat stacked-type conductive polymer actuator in accordance with the second embodiment of the present invention.
Figure 4B:
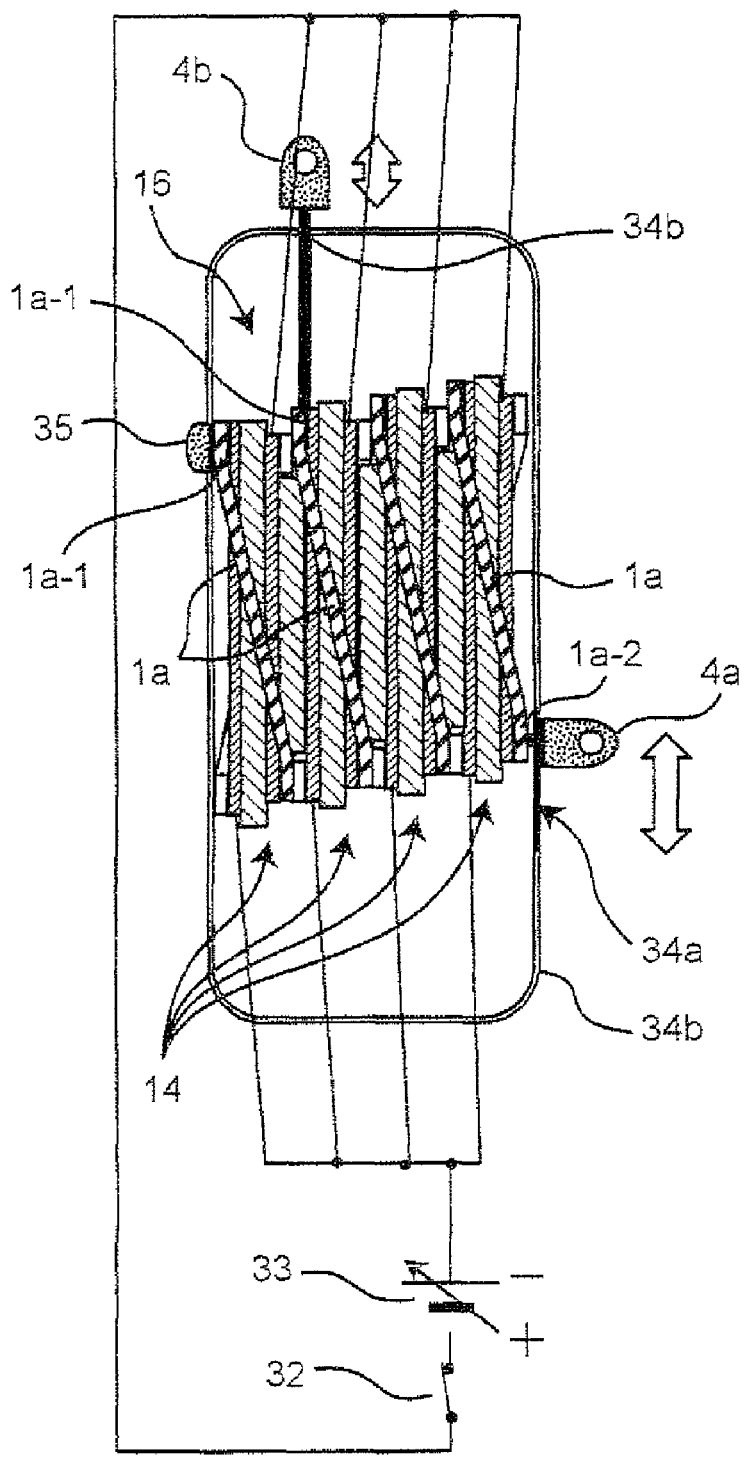
FIG. 4B is a view that shows a structure for use in externally outputting a driving force of the flat stacked-type conductive polymer actuator in accordance with the second embodiment of the present invention.

FIGS. 4A and 4B respectively show a structure in which the actuator 16 is housed in a casing 34 provided with an output unit 4a, and a structure in which the actuator 16 is housed in a casing 34 provided with output units 4a and 4b, in order to output the increased displacement outside the actuator 16 as a driving force. The amounts of displacements are different from each other for the first fixing member 1a and the second fixing member 1b to which the output unit 4a or 4b is formed.

In FIG. 4A, the outer surface of the first end portion 1a-1 of the first fixing member 1a of the actuator 14 on one end portion (left end portion in FIG. 4A) of the actuator 16 is secured to the casing 34 with a securing member 35, and the output unit 4a, which is secured to the outer surface, in a manner so as to protrude therefrom, of the second end portion 1b-2 of the second fixing member 1b of the actuator 14 on the other end portion (right end portion in FIG. 4A) of the actuator 16, is allowed to externally protrude from the casing 34 through an opening 34a provided in the casing 34. Therefore, when the actuator 16 is driven, the output unit 4a is allowed to freely move in the vertical direction in FIG. 4A with respect to the casing 34 by the displacement of the actuator 16.

Moreover, in FIG. 4B, the outer surface of the first end portion 1a-1 of the first fixing member 1a of the actuator 14 on one end portion (left end portion in the figure) of the actuator 16 is secured to the casing 34 with the securing member 35, and the output unit 4a, which is secured to the outer surface, in a manner so as to protrude therefrom, of the second end portion 1a-2 of the first fixing member 1a of the actuator 14 on the other end portion (right end portion in the figure) of the actuator 16, is allowed to externally protrude from the casing 34 through the opening 34a in the casing 34. Furthermore, the output unit 4b, which is secured to the first end portion 1a-1 of the first fixing member 1a of the second actuator 14 from the one end portion (left end portion in the figure) of the actuator 16 in a manner so as to protrude therefrom along the longitudinal direction orthogonal to the thickness direction thereof, is allowed to externally protrude from the casing 34 through an opening 34b provided in the casing 34. Therefore, when the actuator 16 is driven, the output unit 4a and the output unit 4b are allowed to freely move in the vertical direction in FIG. 4B with respect to the casing 34 by the displacement of the actuator 16.

Figure 4C:
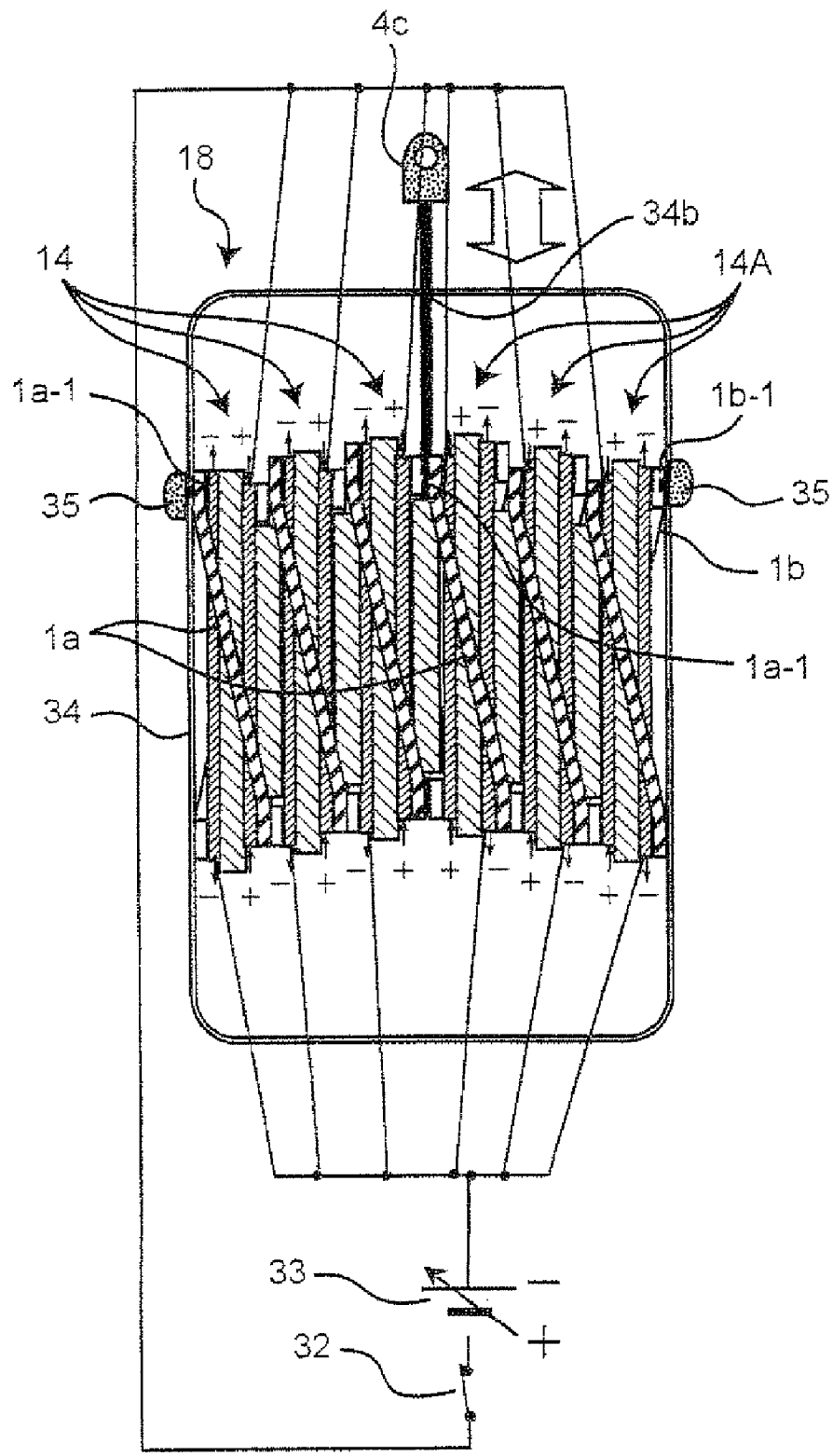
FIG. 4C is a view that shows a structure for use in externally outputting a driving force of the flat stacked-type conductive polymer actuator in accordance with the second embodiment of the present invention.

FIG. 4C shows an example of combination in which the polarity of an electric potential difference to be applied between the first conductive polymer film 2a and the second conductive polymer film 2b of each of the actuators 14 is reversed at a half position of an entire staked actuator 18.

More specifically, the actuator 18 is configured by the actuators 14 described above and actuators 14A of each of which polarity of the electric potential difference is reversed. The outer surface of the first end portion 1*a*-1 of the first fixing member 1*a* of the actuator 14 on one end portion (left end portion in FIG. 4C) of the actuator 18 and the casing 34 are secured to each other with the securing member 35. The outer surface of the first end portion 1*b*-1 of the second fixing member 1*b* of the actuator 14A on the other end portion (right end portion in FIG. 4C) of the actuator 18 and the casing 34 are secured to each other with the securing member 35. Moreover, an output unit 4*c*, which is secured to a connecting portion between the outer surface of the first end portion 1*b*-1 of the second fixing member 1*b* of the third actuator 14 from the left side and the outer surface of the first end portion 1*a*-1 of the first fixing member 1*a* of the fourth actuator 14 from the left side, that is, a coupling portion between the three actuators 14 on the left side and the three actuators 14 on the right side in FIG. 4C, is allowed to externally protrude from the casing 34 along the longitudinal direction thereof through the opening 34*b* of the casing 34. In this structure, the actuators are allowed to freely move in the vertical direction with respect to the casing 34. The total number of the first conductive polymer films 2*a* and the second conductive polymer films 2*b* formed as shown in FIG. 4C is two times as many as that of the structure shown in FIG. 4A; however, the effect of the increased displacements is half (that is, one time) so that the displacement is the same as that of the output unit 4*a* in FIG. 4A. Nevertheless, the driving force of the output unit 4*c* is two times higher than that of the output unit 4*a*. This example shows that such an application is available.

In accordance with this structure, the individual displacements of the first fixing members 1*a* and the second fixing members 1*b* are added by being connected to each other by the adhesive agent 17, and the total amount of displacements is subsequently increased so that it is possible to provide the flat stacked-type conductive polymer actuator 18 having a large amount of displacement.

In the second embodiment, a bonding agent is used as the adhesive agent 17 for connecting the actuators 14 each serving as one constituent unit; alternatively, there may be adopted another mechanical connecting method of installing another sandwiching member. That is, as modified examples for the adhesive agent, the modified examples as described in the first embodiment can also be applied to the second embodiment.

The electrolyte retention layer 3 is prepared by impregnating the separator with the ionic liquid so as to prevent electric short circuiting between the adjacent first conductive polymer film 2*a* and the second conductive polymer film 2*b*; alternatively, another method may be used in which beads are mixed therein so as to prevent electric short circuiting with the lubricating characteristic being maintained, or in which the separator is not provided by using the gelled ionic solution.

Third Embodiment

FIGS. 5A to 5F are views that show a structure of a flat stacked-type conductive polymer actuator 46 in accordance with a third embodiment of the present invention. In FIGS. 5A to 5F, the same components as those of FIGS. 1A to 4C are indicated by the same reference symbols, and the description thereof will not be repeatedly provided.

In FIGS. 5A, 5B, 5C, and 5D, the first fixing member 1*a* and the second fixing member 1*b* provided in the first embodiment are respectively prepared as rectangular plate-shaped first and second porous members 3*a* and 3*b*, and by respectively injecting an ionic solution into the first and second porous members 3*a* and 3*b*, the respective members are allowed to exert the same function as that of the electrolyte retention layer 3. Peripheral portions (for example, long side portions (two side edge portions in FIGS. 5A and 5C) 3*as* and 3*bs* along the longitudinal direction) of the first and second porous members 3*a* and 3*b* are allowed to contain a curing agent to increase the strength so as to prevent buckling or the like. In this case, as shown in FIGS. 5A, 5B, 5C, and 5D, peripheral portions (for example, short side portions (upper end portions in FIGS. 5A, 5B, 5C, and 5D) along the width direction) 3*ad* and 3*bd* in the width direction of the first and second porous members 3*a* and 3*b* are allowed to contain a curing agent, which will be described later.

Figure 5A:
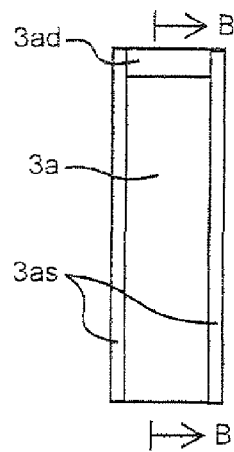
FIG. 5A is a view that shows a structure of a flat stacked-type conductive polymer actuator in accordance with a third embodiment of the present invention.
Figure 5B:
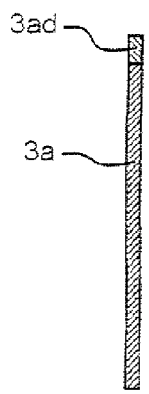
FIG. 5B is a B-B line cross-sectional side view of FIG. 5A.
Figure 5C:
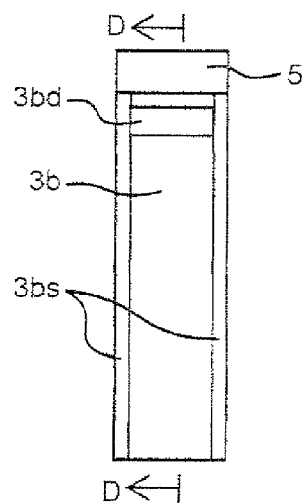
FIG. 5C is a view that shows a structure of the flat stacked-type conductive polymer actuator in accordance with the third embodiment of the present invention.
Figure 5D:
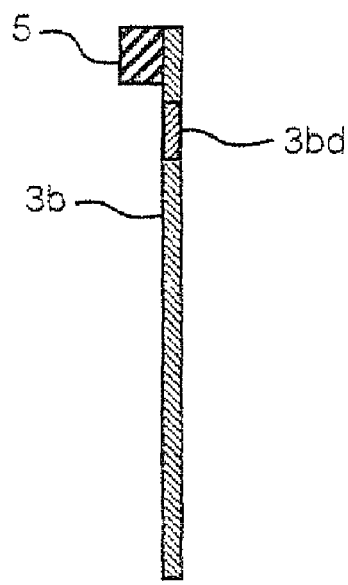
FIG. 5D is a D-D line cross-sectional side view of FIG. 5C.
Figure 5E:
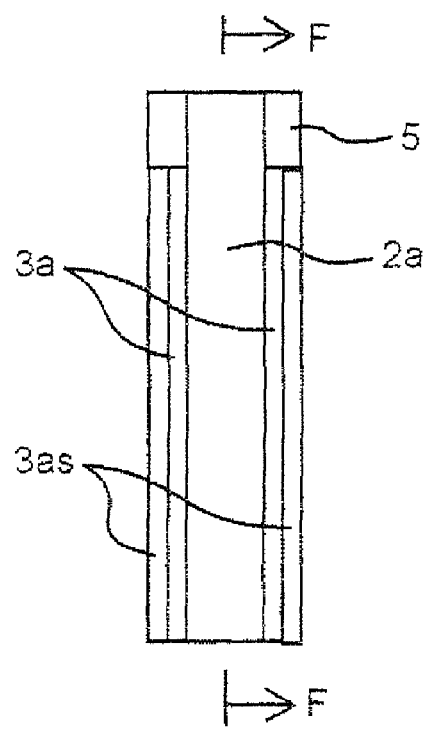
FIG. 5E is a view that shows a structure of the flat stacked-type conductive polymer actuator in accordance with the third embodiment of the present invention.
Figure 5F:
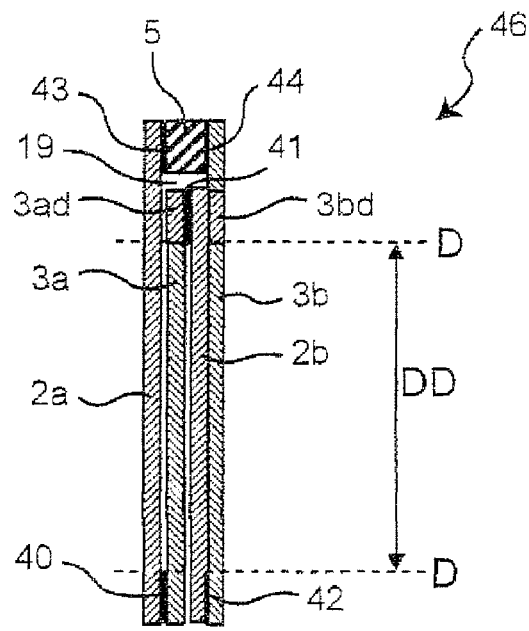
FIG. 5F is an F-F line cross-sectional side view of FIG. 5E.

Next, as shown in FIG. 5F, connections having a zigzag pattern among the first and second porous members 3*a*, 3*b*, the first conductive polymer film 2*a*, and the second conductive polymer film 2*b* are made by using adhesive agents 40, 41, and 42, and, in particular, the connection between the second porous member 3*b* and the first conductive polymer film 2*a* is made by using an adhesive agent 43 with a spacer 5 interposed therebetween so as to maintain a gap. That is, in FIG. 5F, the inner surface on the lower end portion of the first conductive polymer film 2*a* and the outer surface on the lower end portion of the first porous member 3*a* are connected to each other with the adhesive agent 40 being interposed therebetween. The inner surface of the peripheral portion 3*ad* in the width direction of containing the curing agent on the upper end portion of the first porous member 3*a* and the opposed surface on the upper end portion of the second conductive polymer film 2*b* are connected to each other with the adhesive agent 41 being interposed therebetween. The outer surface on the lower end portion of the second conductive polymer film 2*b* and the inner surface on the lower end portion of the second porous member 3*b* are connected to each other with the adhesive agent 42 being interposed therebetween. With a gap 19 being provided between the spacer 5 and the upper end of the first porous member 3*a* as well as the upper end of the second conductive polymer film 2*b*, the inner surface on the upper end portion of the first conductive polymer film 2*a* is connected to one of the outer surfaces of the spacer 5 with the adhesive agent 43 being interposed therebetween. The inner surface on the upper end portion of the second porous member 3*b* is connected to the other outer surface of the spacer 5 with an adhesive agent 44 being interposed therebetween. Therefore, the dimensions in the longitudinal direction of the first porous member 3*a* and the second conductive polymer film 2*b* are substantially the same, and the dimensions in the longitudinal direction of the second porous member 3*b* and the first conductive polymer film 2*a* are substantially the same, while the dimensions in the longitudinal direction of the first porous member 3*a* and the second conductive polymer film 2*b* are made shorter than the dimensions in the longitudinal direction of the second porous member 3*b* and the first conductive polymer film 2*a*. The dimensions in the width direction of the first porous member 3*a* and the second porous member 3*b* are the same, and the dimensions in the width direction of the first conductive polymer film 2*a* and the second conductive polymer film 2*b* are the same, while the dimensions in the width direction of the first conductive polymer film 2*a* and the second conductive polymer film 2*b* are made smaller than the dimensions in the width direction of the first porous member 3*a* and the second porous member 3*b*. The dimension in the width direction of the spacer 5 is the same as the dimensions in the width direction of the first porous member 3*a* and the second porous member 3*b*. The thickness of the spacer 5 is made substantially the same as the total of the thickness of the first porous member 3a, the thickness of the second conductive polymer film 2b, and the thicknesses of the adhesive agents 40, 41, and 42, or made larger than the above (for example, a dimension larger by about several tens μm). This point will be described later.

Moreover, in FIG. 5F, it is important to set the amounts of displacements of the first conductive polymer film 2a and the second conductive polymer film 2b to be equal to each other. Although the materials for the respective members and the thicknesses of the films also serve as parameters that are influenced by the amounts of displacements, what most influences is the length of the contact portion between the first and second porous members 3a and 3b. In FIG. 5F, a distance DD indicated by two broken lines D represents the length of portions (in other words, expandable portions except for the bonded and secured portions by the adhesives) in which the first conductive polymer film 2a and the second conductive polymer film 2b are expanded or contracted. At the portion where the adhesive agent 40, 41, or 42 is located, it is difficult for an ionic solution to pass therethrough, and such a portion is secured, this portion cannot be expanded or contracted. Moreover, no ionic solution can be provided on the two side edge portions 3as and 3bs that contain the curing agent in the first and second porous members 3a and 3b. In order to prevent expansion/contraction at the portions other than the distance DD, a curing agent is contained in the connecting portion (that is, the peripheral portion in the width direction on the upper end portion of the first porous member 3a) 3ad of the first porous member 3a with the second conductive polymer film 2b by the adhesive agent 41. As a result, only the distance DD has a length in which the first conductive polymer film 2a and the second conductive polymer film 2b are made in contact with the ionic solution and are capable of expanding/contracting, and the flat stacked-type conductive polymer actuator 46 of the third embodiment can be driven by the amounts of displacements of the first conductive polymer film 2a and the second conductive polymer film 2b in the portions of this length.

Figure 6A:
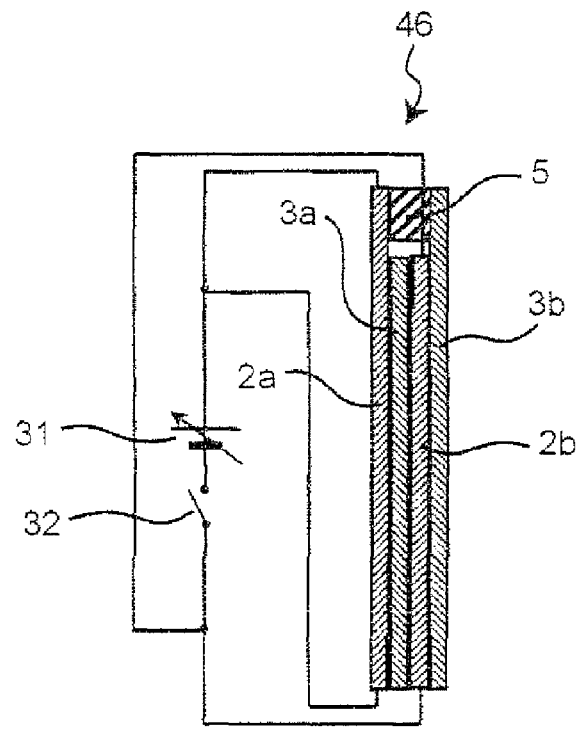
FIG. 6A is a view for describing a voltage and a direction of a displacement of the flat stacked-type conductive polymer actuator in accordance with the third embodiment of the present invention.
Figure 7A:
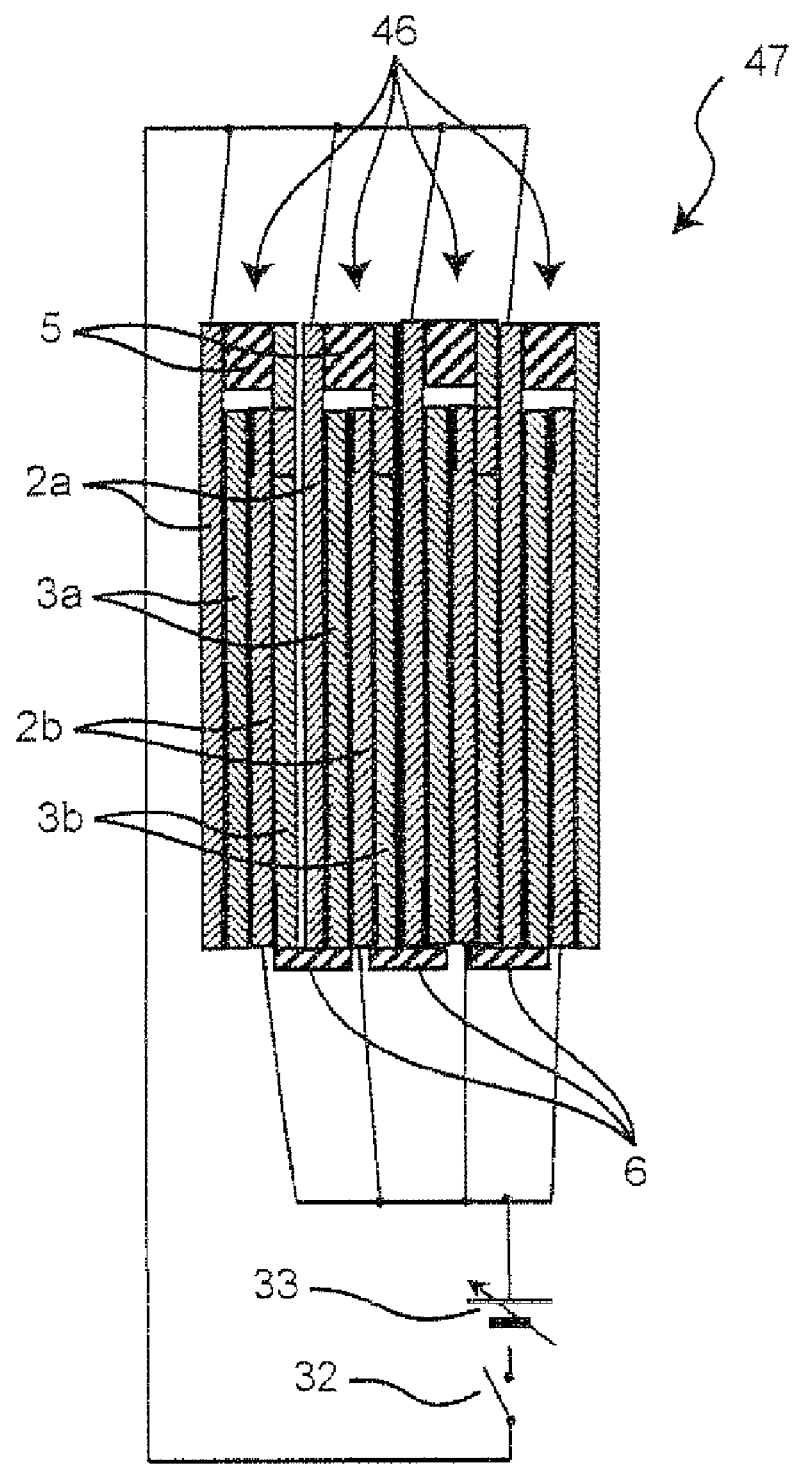
FIG. 7A is a view that shows a structure for use in externally outputting a driving force of the flat stacked-type conductive polymer actuator in accordance with the third embodiment of the present invention.
Figure 7B:
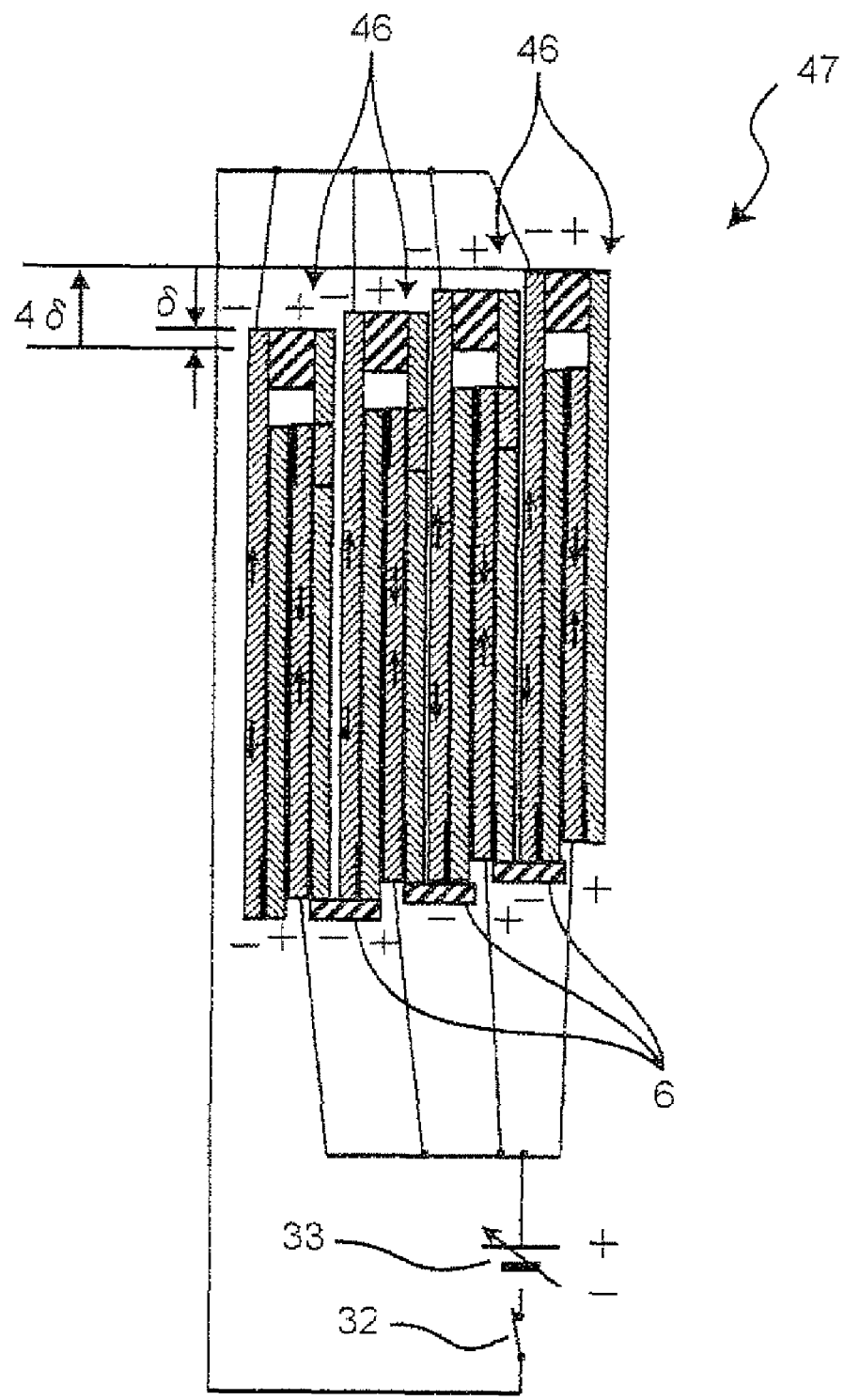
FIG. 7B is a view that shows a structure for use in externally outputting a driving force of the flat stacked-type conductive polymer actuator in accordance with the third embodiment of the present invention.
Figure 7C:
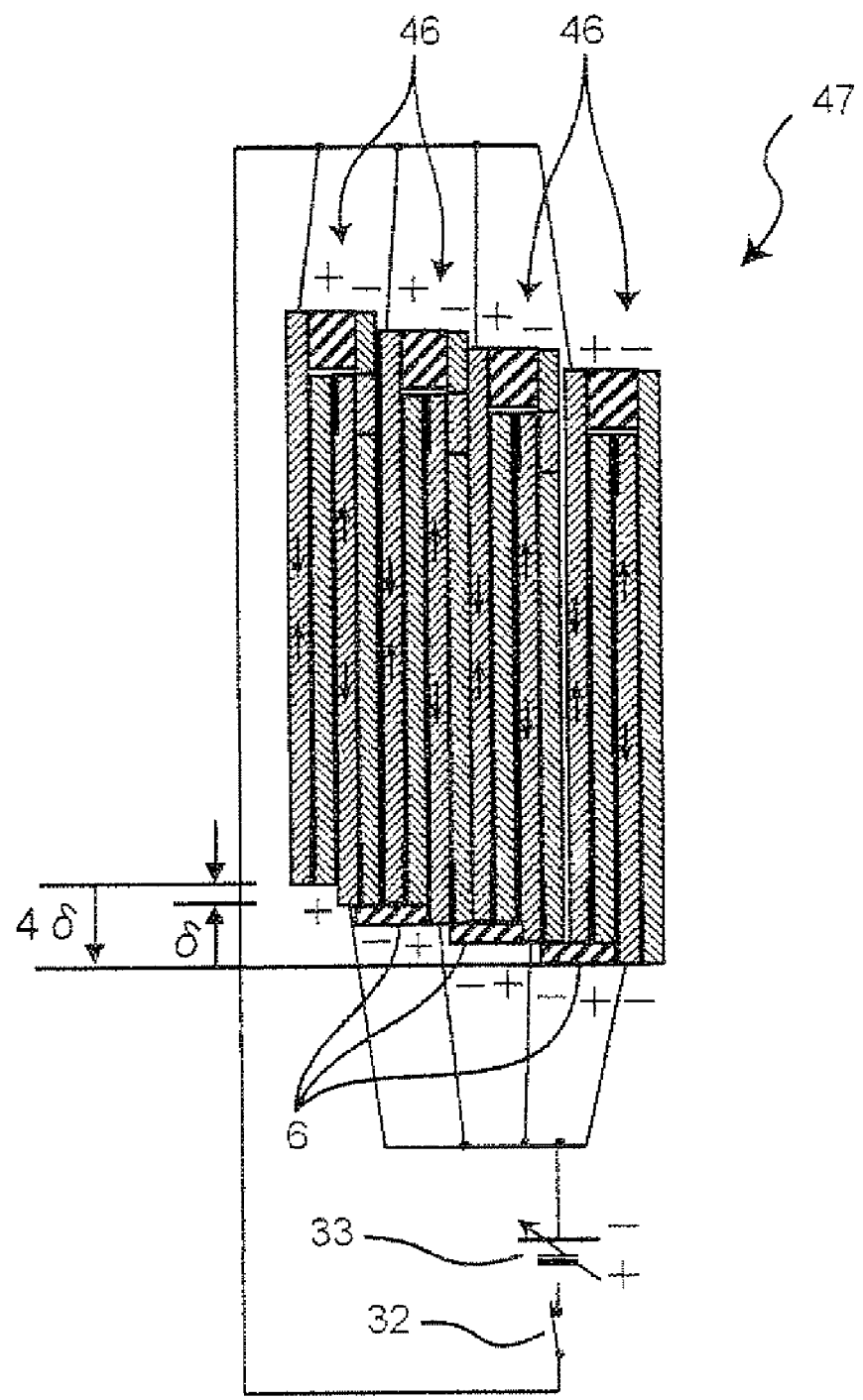
FIG. 7C is a view that shows a structure for use in externally outputting a driving force of the flat stacked-type conductive polymer actuator in accordance with the third embodiment of the present invention.

Moreover, in order to effectively use the expanding/contracting operation in this distance DD also in a structure in which, as shown in FIGS. 7A to 7C to be described later, a plurality of actuators 46 are disposed adjacent with one another to form an actuator 47, as shown in FIG. 5F, a curing agent is contained in a portion 3bd, which is opposed to the portion (upper end portion of the second conductive polymer film 2b) in the second porous member 3b where the first porous member 3a and the second conductive polymer film 2b are connected to each other by the adhesive agent 41. In a case where the plurality of actuators 46 are disposed not to be adjacent to one another as shown in FIGS. 7A to 7C, it is not necessary to allow the portion 3bd to contain the curing agent therein as shown in FIG. 6A and the like.

FIG. 6A shows a structure in which the switch 32 and the variable DC power supply 33 are installed so that an electric potential difference is applicable between the first conductive polymer film 2a and the second conductive polymer film 2b of the actuator 46 in FIG. 5F. That is, the switch 32 and the variable DC power supply 33 are installed between the two ends (for example, upper and lower ends) in the longitudinal direction of the first conductive polymer film 2a and the two ends (for example, upper and lower ends) in the longitudinal direction of the second conductive polymer film 2b of the flat conductive polymer actuator 46, so that the actuator 46 can be driven, that is, the electric potential difference is applied across the first conductive polymer film 2a as well as across the second conductive polymer film 2b.

Figure 6B:
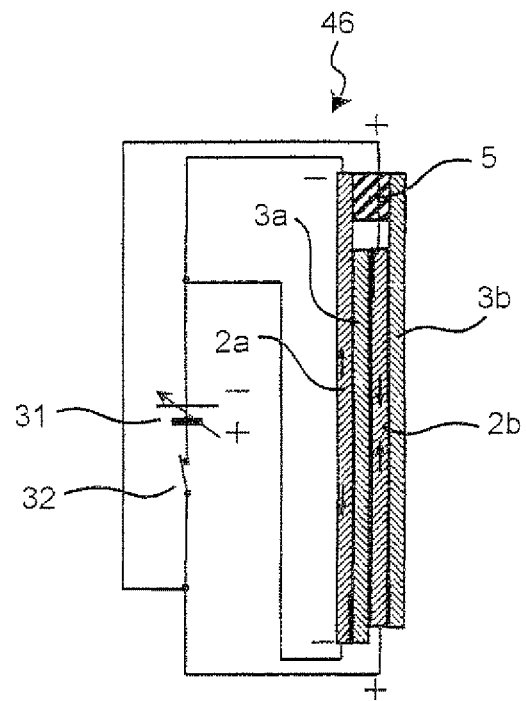
FIG. 6B is a view for describing a voltage and a direction of a displacement of the flat stacked-type conductive polymer actuator in accordance with the third embodiment of the present invention.
Figure 6C:
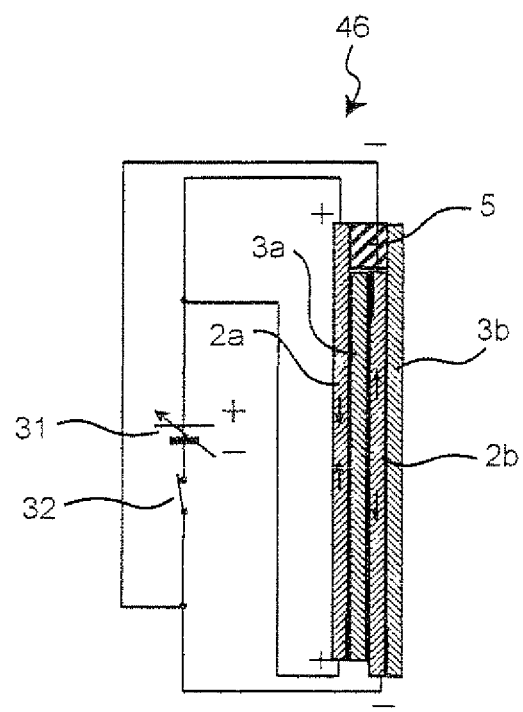
FIG. 6C is a view for describing a voltage and a direction of a displacement of the flat stacked-type conductive polymer actuator in accordance with the third embodiment of the present invention.

In this structure, as shown in FIGS. 6B and 6C, one of the first conductive polymer film 2a and the second conductive polymer film 2b is expanded or contracted, while the other conductive polymer film is contracted or expanded, by an oxidation-reduction reaction. As a result, as shown in FIGS. 6A to 6C, by the displacements of the first and second porous members 3a and 3b, a driving force of the actuator 46 can be externally outputted, similarly to the first embodiment and the second embodiment.

Alternatively, as shown in FIGS. 7A to 7C, the plurality of actuators 46 may be disposed adjacent to one another in parallel therewith, and the second porous member 3b of one of the pair of adjacent actuators 46 may be connected to the first porous member 3a of the other actuator 46 by a link member 6 having a plate shape and rigidity.

In this structure, out of the paired adjacent actuators 46 which face each other with the second porous member 3b of one actuator 46 (for example, the actuator 46 on the left end) being interposed therebetween, an oxidation-reduction reaction is also generated due to an electric potential difference between the second conductive polymer film 2b of one actuator 46 (for example, the actuator 46 on the left end) and the first conductive polymer film 2a of the other actuator 46 (for example, the second actuator 46 from the left end). Accordingly, the amount of displacement by the expansion and contraction of the first conductive polymer film 2a and the second conductive polymer film 2b are increased. In this case, supposing that a displacement between the paired first conductive polymer film 2a and second conductive polymer film 2b in one actuator 46 is set to δ, the four pairs of actuators 46 are respectively connected to one another by using the link members 6 so that a displacement is increased to δ×4=4δ.

Unlike the wiring in FIGS. 6A to 6C, in the wiring from the variable DC power supply 33 in FIGS. 7A to 7C, the switch 32 and the variable DC power supply 33 are connected only to either one of one end (for example, the upper end) in the longitudinal direction of the first conductive polymer film 2a of each actuator 46 and the other end (for example, the lower end) in the longitudinal direction of the second conductive polymer film 2b of each actuator 46. This arrangement is made so as to prevent a short circuiting of each of + or − wiring due to increase in wirings; however, since the first conductive polymer film 2a and the second conductive polymer film 2b have sufficient conductivity, the influence to the amount of displacement is small.

As the respective materials for the first and second porous members 3a and 3b, there may be used a filter material or the like having an aperture ratio of from 0.1 μm to 0.5 μm, with the base material of PVDF (polyvinylidene fluoride) or the like. In this case, as an example, a filter material having an aperture ratio of 0.45 μm can be used. Alternatively, as a similar filter material, Teflon (registered trademark) is also available; however, the use of this material makes it difficult to select the curing agent or the adhesive agent to be described later.

As the curing agent for use in forming the two side edge portions 3as and 3bs containing the curing agent, in the same manner as in the adhesive agents 40, 41, 42, and 43, an epoxy-based adhesive agent that has been widely used may be applied in the same manner as in the adhesive agents 10, 11, 12, and 13. As the curing agent for use in forming the peripheral portions 3ad and 3bd in the width direction of the first and second porous materials 3a and 3b as well, the epoxy-based adhesive agent may be used.

Furthermore, as the adhesive agent 44, the epoxy-based adhesive agent can be used in the same manner.

As the spacer 5 and the link member 6, a plate member made of PVDF (polyvinylidene fluoride) may be used; alternatively, this plate member may be substituted with a porous filter.

With respect to the materials same as those of the first embodiment, the description thereof will not be repeatedly provided.

The above-mentioned materials are only exemplified, and the present invention is not intended to be limited by these materials.

In accordance with this structure, the first fixing member 1a and the second fixing member 1b are configured by the first and second porous members 3a and 3b, with the first and second porous members 3a and 3b being allowed also to function as the electrolyte retention layer 3, so that the electrolyte retention layer 3 is not required. The number of constituent parts is reduced to result in reduction of the thickness of the entire actuator; thus, even in the case of a stacked structure with a large amount of displacement, it is possible to provide the flat stacked-type conductive polymer actuator the entire thickness of which can be made thinner. Moreover, by increasing the number of the flat stacked-type conductive polymer actuators adjacent to one another, the individual displacements can be added to increase the amounts of entire displacements, so that the flat stacked-type conductive polymer actuator 46 having a large amount of displacement can be provided.

Figure 8A:
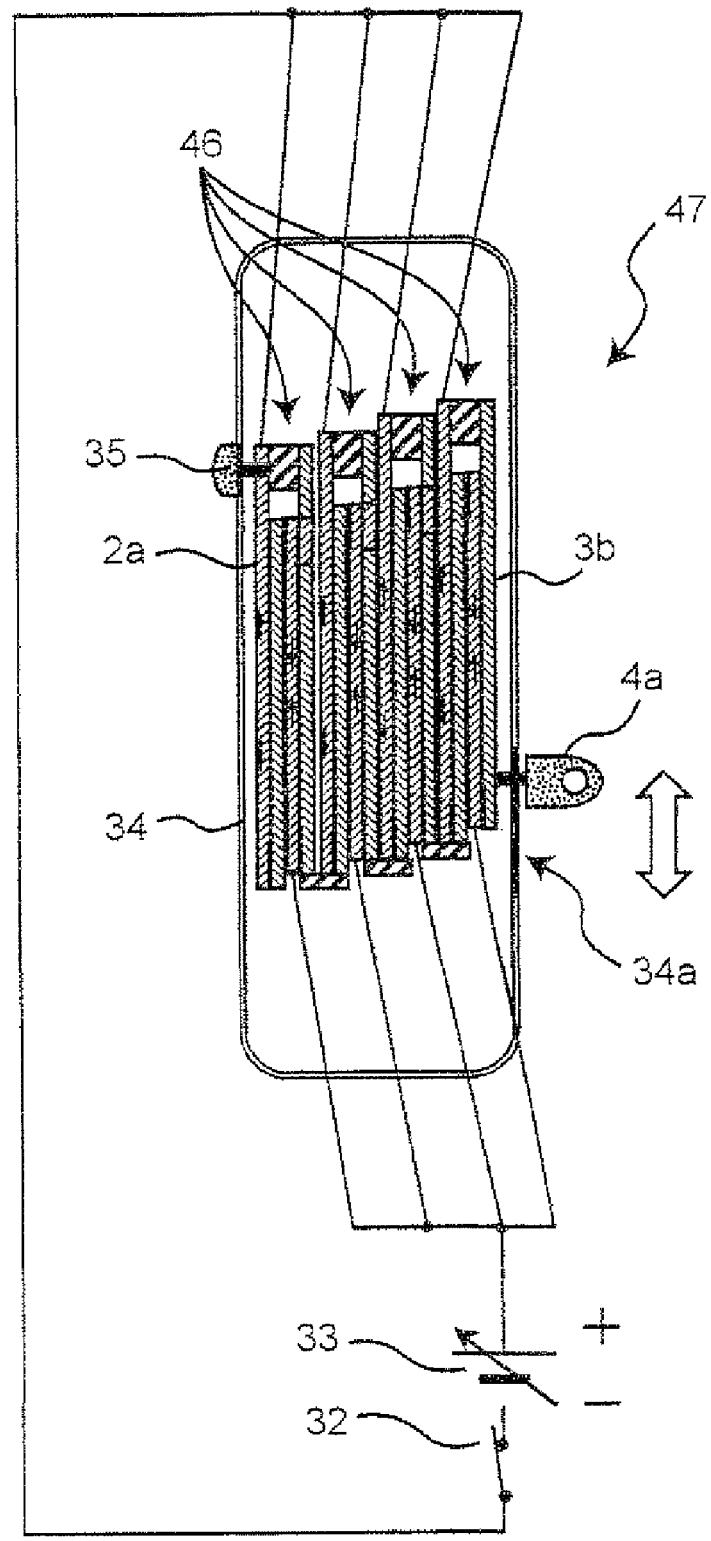
FIG. 8A is a view that shows a structure for use in externally outputting a driving force of the flat stacked-type conductive polymer actuator in accordance with the third embodiment of the present invention.
Figure 8B:
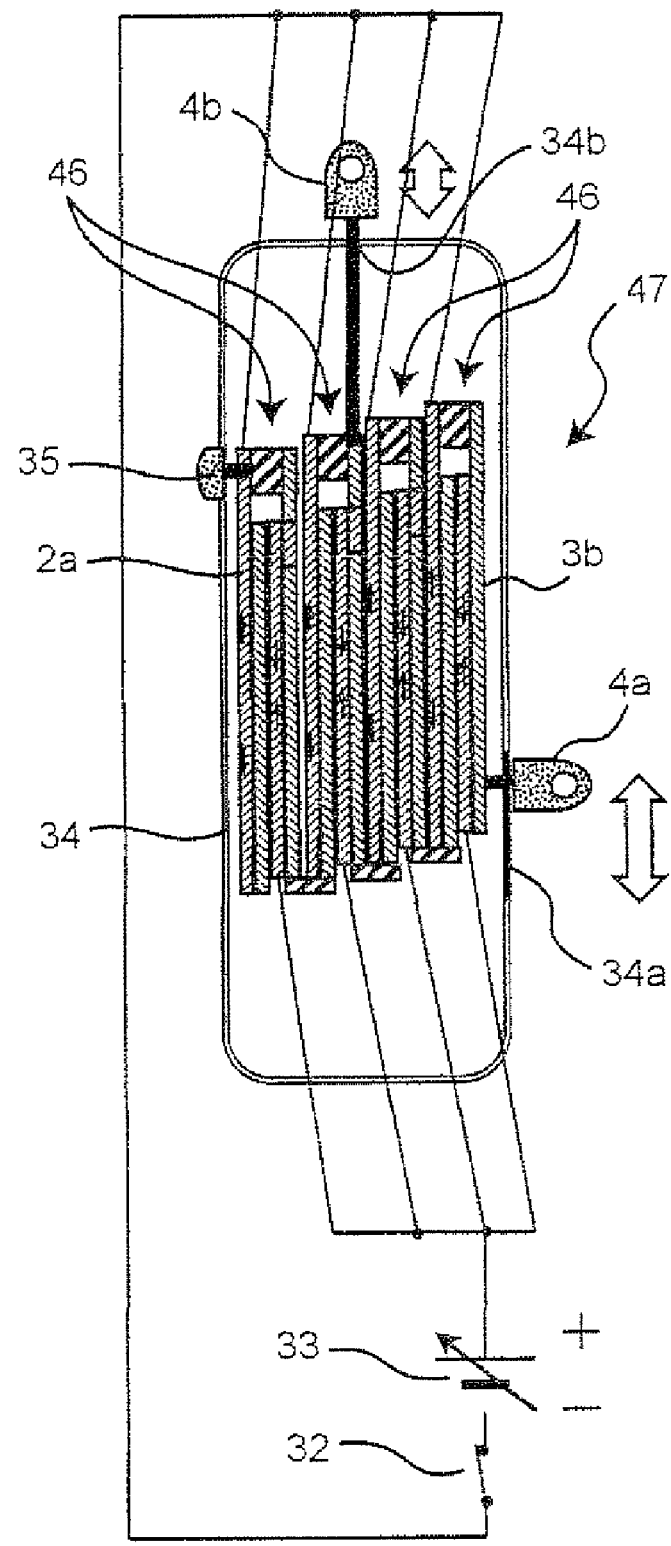
FIG. 8B is a view that shows a structure for use in externally outputting a driving force of the flat stacked-type conductive polymer actuator in accordance with the third embodiment of the present invention.
Figure 8C:
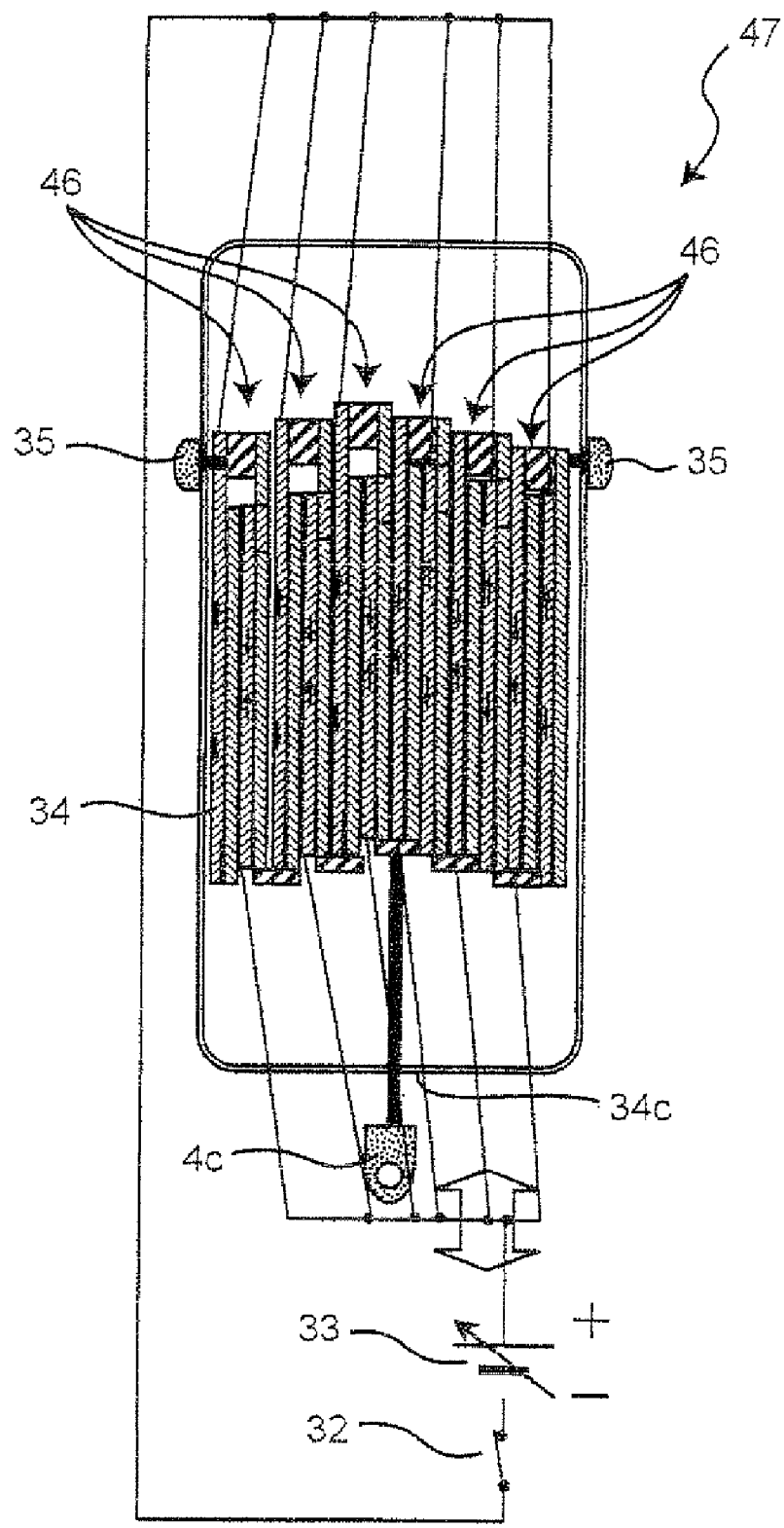
FIG. 8C is a view that shows a structure for use in externally outputting a driving force of the flat stacked-type conductive polymer actuator in accordance with the third embodiment of the present invention.

The resulting structure in which a driving force of the flat stacked-type conductive polymer actuator 46 in the third embodiment is externally outputted is shown in FIGS. 8A to 8C. More specifically, FIGS. 8A to 8C show a structure in which the actuators 46 are respectively housed in a casing 34 provided with the output unit 4a, 4b, or 4c so as to externally output the above-mentioned large amount of displacement from the actuators 46 as a driving force. The amount of displacement is different depending on the second porous member 3a provided with the output unit 4a, the second porous member 3a provided with the output units 4a and 4b, and the link member 6 provided with the output unit 4c.

In FIG. 8A, one end portion (upper end portion) of the first conductive polymer film 2a of the actuator 46 on one end portion (left end portion in FIG. 8A) of the actuator 47 and the casing 34 are secured to each other by using the securing member 35, and the output unit 4a secured to the outer surface of the other end portion (lower end portion), in a manner so as to protrude therefrom, of the second porous member 3b of the actuator 46 on the other end portion (right end portion in FIG. 8A) of the actuator 47 is allowed to externally protrude from the casing 34 through the opening 34a in the casing 34. Therefore, when the actuator 46 is driven, the output unit 4a is allowed to freely move in the vertical direction in FIG. 8A with respect to the casing 34 by the displacement of the actuator 46.

Moreover, in FIG. 8B, one end portion (upper end portion) of the first conductive polymer film 2a of the actuator 46 on one end portion (left end portion in FIG. 8B) of the actuator 46 and the casing 34 are secured to each other by using the securing member 35, and the output unit 4a, which is secured to the outer surface on the other end portion (lower end portion), in a manner so as to protrude therefrom, of the second porous member 3b of the actuator 46 on the other end portion (right end portion in FIG. 8B) of the actuator 47, is allowed to externally protrude from the casing 34 through the opening 34a in the casing 34. Moreover, the output unit 4b, which is secured to one end portion (upper end portion in FIG. 8B) of the second porous member 3b of the second actuator 46 from one end portion (left end portion in FIG. 8B) of the actuator so as to protrude along the longitudinal direction orthogonal to the thickness direction thereof, is allowed to externally protrude from the casing 34 through the opening 34b in the casing 34. Therefore, when the actuator 47 is driven, the output unit 4a and the output unit 4b are allowed to freely move in the vertical direction in FIG. 8A with respect to the casing 34 by the displacement of the actuator 47.

In FIG. 8C, one end portion (upper end portion) of the first conductive polymer film 2a of the actuator 46 on one end portion (left end portion in FIG. 8B) of the actuator 46 and the casing 34 are secured to each other by using the securing member 35, and one end portion (upper end portion) of the second porous member 3b of the actuator 46 on the other end portion (right end portion in FIG. 8B) of the actuator 47 and the casing 34 are secured to each other by using the securing member 35. Moreover, the output unit 4c, which is secured to the link member 6 of the third actuator 46 from one end portion (left end portion in FIG. 8B) of the actuator 47, in a manner so as to protrude along the longitudinal direction orthogonal to the thickness direction thereof, is allowed to externally protrude downward from the casing 34 through an opening 34c in the casing 34. Therefore, when the actuator 47 is driven, the output unit 4c is allowed to freely move in the vertical direction in FIG. 8C with respect to the casing 34 by the displacement of the actuator 47.

Unlike the structures in FIGS. 4A to 4C in the second embodiment described above, this structure is significantly characterized in that, by making the thickness of the entire flat stacked-type conductive polymer actuator thinner, the casing 34 is also made thinner.

In the third embodiment, upon the connections among the first and second porous members 3a and 3b and the first and second conductive polymer films 2a and 2b, the adhesive agents 40, 41, 42, and 43 are used; alternatively, without using the adhesive agents, these connections may be achieved upon curing in the casting process of forming the first conductive polymer film 2a and the second conductive polymer film 2b or upon deposition in the electrochemical polymerization process for the first conductive polymer film 2a and the second conductive polymer film 2b. Alternatively, by installing an additional member, a mechanical connecting method or the like may be adopted in which the first conductive polymer film 2a, the second conductive polymer film 2b, and the first and second porous members 3a and 3b are sandwiched.

In the structure in FIG. 5F, the thickness of the spacer 5 shown in FIG. 5D is desirably set to the total or more of the thicknesses of the first porous member 3a and the second conductive polymer film 2b positioned between the first conductive polymer film 2a and the second porous member 3b. In a case of being less than the total thickness, since the first conductive polymer film 2a, the first porous member 3a, the second conductive polymer film 2b, and the second porous member 3b are made in contact with one another with a pressure being applied thereto, with a result that the resistance upon expansion/contraction is rapidly increased to cause a reduction in the amounts of displacements. In order to prevent the reduction, the contacts are desirably achieved so as to allow a minute gap having about several tens μm to be provided as each of the gaps.

In one actual example of the third embodiment, the conductive polymer films 2a, 2b, each having 15 μm in thickness, are used in the same manner as in the first embodiment. Moreover, when using a porous Teflon (registered trademark) material as the porous members 3a and 3b, the members have a thickness of about 100 μm. In other words, the thickness of each of the first conductive polymer film 2a and the second conductive polymer film 2b is 15 μm. Also taking into consideration that the aforementioned minute gaps having about several tens µm are to be provided, the thickness of the structure in FIG. 5E is 250 µm, which is obtained by adding 20 µm to 230 µm.

Although the curing agent is contained in at least a part of the peripheral portion of each of the first and second porous members 3a and 3b, there may be adopted another structure in which, in order to prevent buckling due to the increase in strength, an additional member may be formed on the surface of the first or second porous member 3a or 3b.

Working Example 1

Figure 9A:
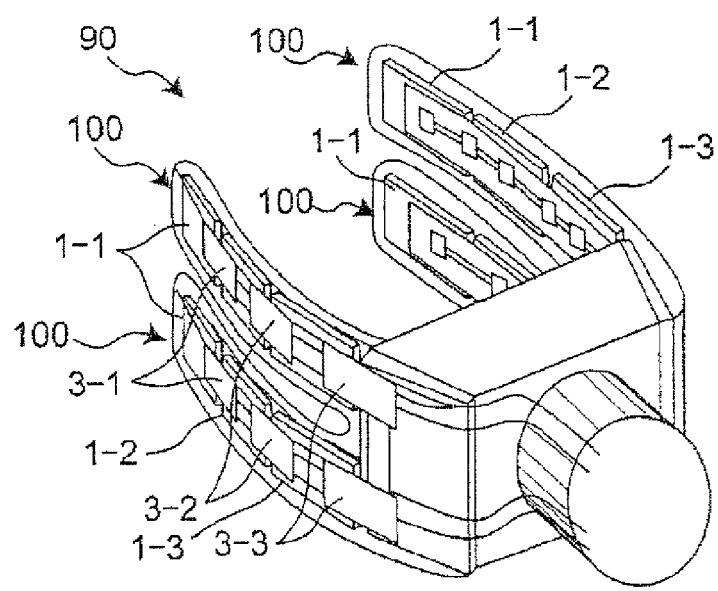
FIG. 9A is a view that shows a working example of the flat stacked-type conductive polymer actuator in accordance with the second embodiment of the present invention.

FIG. 9A shows a structure quoted from FIG. 3A of U.S. Pat. No. 3,723,818 relating to a robot hand 90. Actuators 3-1, 3-2, and 3-3 serving as driving power sources are described therein, and by using the structure such as shown in FIGS. 4A to 4C described above, which is an example of one of the flat stacked-type conductive polymer actuators of the present invention as one of parts of these actuators, in particular, the combination as shown in FIG. 4C as the basic structure thereof, it is possible to provide, in a small space, a large stress that is impossible to achieve with a single conductive polymer film.

Figure 9B:
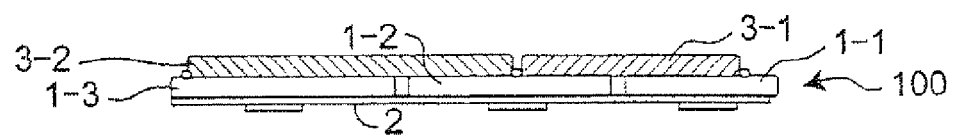
FIG. 9B is a view that shows the working example of the flat stacked-type conductive polymer actuator in accordance with the second embodiment of the present invention.
Figure 9C:
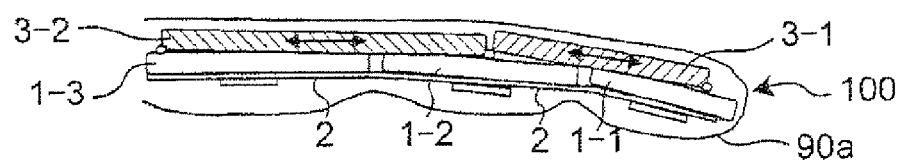
FIG. 9C is a view that shows the working example of the flat stacked-type conductive polymer actuator in accordance with the second embodiment of the present invention.

More specifically, as in a flat multi-joint driving mechanism as shown in FIGS. 9B and 9C, each finger 100 can be extended and bent by expanding and contracting actuators the 3-1 and 3-2. In this structure, increases in the stress and in the amount of displacement are required as the flat stacked-type conductive polymer actuator, as will be described later. Bone members 1-1, 1-2, and 1-3, as well as a coupling member 2 are further included so that the finger 100 can be bent by a torque in the thickness direction thereof.

Figure 9D:
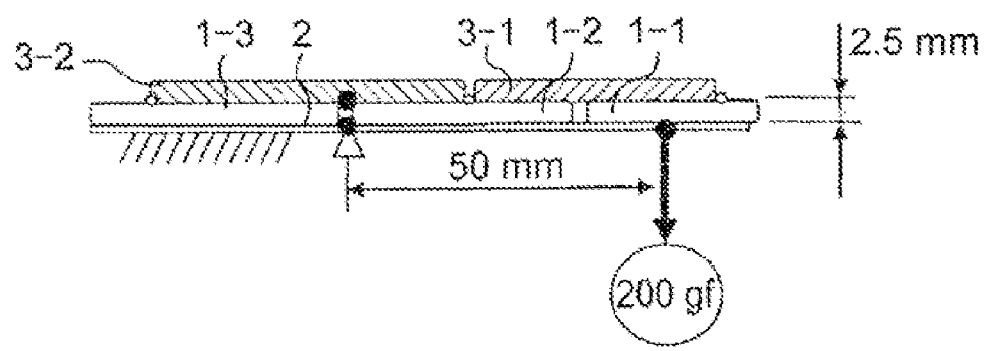
FIG. 9D is a view that shows the working example of the flat stacked-type conductive polymer actuator in accordance with the second embodiment of the present invention.
Figure 9D:
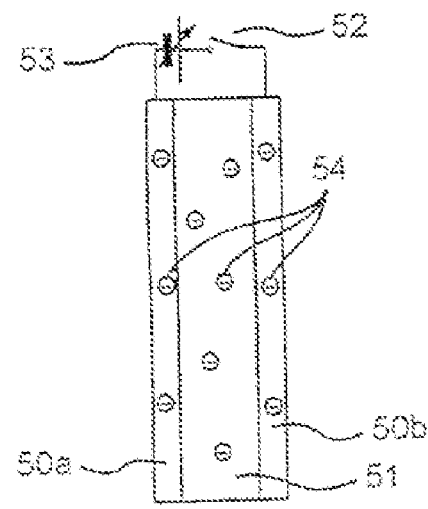

In order to describe in more detail, the flat multi-joint driving mechanism in FIGS. 9B and 9C is shown as a schematic model in FIG. 9D with specific dimensions indicated therein. By using this model, described below is an example of actual designing numeric values. Suppose that an object of 100 gf is grabbed by this robot hand as a lightweight object. A grabbing force required therefor is assumed to be about 20 gr, although it depends also on the surface material for the robot hand. As a result, based upon a distance of 2.5 mm between fulcrums in the thickness direction relative to a distance of 50 mm between the load and the fulcrums, a displacement expansion rate in the flat multi-joint driving mechanism is regarded as 20 times. Consequently, since the stress is one-twentieth thereof, a stress of 400 gf is required to be exerted from the actuator 3-2 in order to output the grabbing force of 20 gf. In contrast, supposing that the required amount of displacement for the grabbing operation is about 10 mm per joint, only 0.5 mm, that is, one-twentieth, is required as the amount of displacement of the actuator 3-2.

On the other hand, the structure shown in FIG. 4C is used as the flat stacked-type conductive polymer actuator. In FIG. 4C, in order to provide the stress and the amount of displacement required to the grabbing operation, three flat stacked-type conductive polymer actuators each having the structure shown in FIG. 1 are used in the structure shown in FIG. 3A, and two sets thereof are used to form the structure shown in FIG. 4C, so that the amount of displacement is made 3 times and the stress is made 2 times; however, in FIG. 9D, ten flat stacked-type conductive polymer actuators each having the structure shown in FIG. 1 are used in the structure shown in FIG. 3A, and five sets thereof are used to form the structure shown in FIG. 4C, so that the amount of displacement is designed to be 0.5 mm, which is ten times higher than the previous amount of displacement, and the stress is designed to be 400 gf, which is five times higher than the previous stress. Since the stress of about 40 gf, for example, can be obtained when the width of the conductive polymer film is set to be 5 mm, a width of 10 mm, which is two times thereof is adopted in FIG. 9A in this case, in order to obtain the stress of about 80 gf, and the generated displacement upon application of a voltage is set to about 2.0% so that, in the case of the length of 25 mm in FIG. 1, an amount δ of displacement of about 500 µm is supposed to be obtained, that is, in the case of one set of the flat stacked-type conductive polymer actuators in FIG. 1, an amount δ of displacement of about 0.05 mm is supposed to be obtained. In this case, the amount of displacement depends on the stress to be applied as an external force and the period of time of the voltage application. Since the period of time of the voltage application greatly influences in this case, the control operation is carried out for the period of time in which a predetermined amount of displacement has been achieved, while allowing the period of time within a range of from one second to one minute.

In the above-mentioned example, the flat stacked-type conductive polymer actuator to be used has approximate dimensions of 10 mm in width and slightly larger than 50 mm in the longitudinal direction, and approximately 14 mm in the thickness direction. With regard to the thicknesses, the thickness of each of the first conductive polymer film 2a and the second conductive polymer film 2b is 15 µm, and the thickness of the electrolyte retention layer 3 is 40 µm, and each of the first fixing member 1a and the second fixing member 1b is made of a Teflon (registered trademark) sheet having a thickness of 100 µm. Since the aforementioned extra margin of about several tens µm is added thereto, the structure in FIG. 1 has a thickness of 290 µm. Since five sets of 10 pieces of the structures each having a thickness of 290 µm, namely, 50 pieces thereof, are used, the total thickness is about 15 mm. In comparison with the size of a human hand, the robot hand 90 is realized with slightly longer and thicker fingers 100.

Moreover, in a case where the structure in FIG. 5E is applied to the flat stacked-type conductive polymer actuator, the length in the thickness direction can be decreased. When a porous Teflon (registered trademark) material is used for the first and second porous members 3a and 3b, the thickness thereof is about 100 µm. More specifically, the thickness of each of the first conductive polymer film 2a and the second conductive polymer film 2b is 15 µm. Since the provision of the aforementioned minute gap of about several tens µm is taken into consideration, by adding 20 µm to 230 µm, the structure in FIG. 5E has a thickness of 250 µm. Since five sets of 10 pieces of the structures each having a thickness of 250 µm, namely, 50 pieces thereof, are used, the total thickness is about 13 mm.

The structure shown in FIG. 9A has four fingers in total, with the two fingers 100 on two sides facing each other. Like a human hand, these four fingers are aligned so as to face a thumb, which may be required to have a stress even with a small amount of displacement while each of the substantially opposed four fingers each have a larger amount of displacement. In this structure, the flat stacked-type conductive polymer actuator focusing on the stress is applied to the thumb, and the other fingers are each set to have the amount of displacement of four times since only the one-fourth of the stress is required thereto, so that the entire hand is well balanced. Also in this case, all the other four fingers substantially opposed to the thumb are not necessarily required to operate simultaneously, and a controlled voltage can be successively applied from the index finger to the little finger. Moreover, it is easily achieve the structure in which each of the fingers may also have joints so as to be successively displaced from the root portion to the tip.

Moreover, needless to say, in a case where there is some margin for the width of the thumb or other fingers and a great stress is required, by simply align in parallel the flat stacked-type conductive polymer actuators in the width direction of the conductive polymer film, the stress can be increased in proportion to the number of the installed actuators By appropriately combining desired embodiments among the various embodiments described above, the respective effects thereof can be obtained.

The flat stacked-type conductive polymer actuator in accordance with the present invention exerts rigidity and a driving force in both of the contracting direction and the expanding direction. The stacked structure achieves the increase in displacement or in stress. The structure in which the surfaces of the conductive polymer films contracted and expanded face each other with the electrolyte retention layer interposed therebetween realizes the actuator which can be efficiently driven while saving energy and spaces. The resulting actuator can be effectively utilized as an artificial muscle actuator or the like, and as a driving unit or the like for use in a robot arm or a robot hand of a robot. Moreover, in addition to these characteristics, since the actuator has the quiet, light-weight, and power saving structure, the actuator is also applicable to a driving unit of a cooling pump for use in a notebook computer or a mobile telephone, or to a lens actuator or the like of a mobile terminal apparatus.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A flat stacked-type conductive polymer actuator comprising:
    a first conductive polymer film, a plate-shaped first porous member, a second conductive polymer film, and a plate-shaped second porous member, which are stacked on one another, wherein
    each of the first porous member and the second porous member has an ionic solution injected thereinto so as to function also as an electrolyte retention layer,
    a first end portion of the first porous member and a first end portion of the second conductive polymer film that are opposed to each other are connected to each other,
    a first end portion of the first conductive polymer film and a first end portion of the second porous member that are opposed to each other are connected to each other with a spacer being interposed therebetween,
    a second end portion of the first porous member and a second end portion of the first conductive polymer film that are opposed to each other are connected to each other,
    a second end portion of the second conductive polymer film and a second end portion of the second porous member that are opposed to each other are connected to each other, and
    by applying an electric potential difference between the first conductive polymer film and the second conductive polymer film, one of the first conductive polymer film and the second conductive polymer film is expanded or contracted and the other conductive polymer film is contracted or expanded by an oxidation-reduction reaction, so that a driving force is externally outputted by displacements of the first porous member and the second porous member.

2. The flat stacked-type conductive polymer actuator according to claim 1, wherein
    the first porous member and the second conductive polymer film have a same length,
    the first conductive polymer film and the second porous member have a same length, and
    the length of the first porous member and the second conductive polymer film is smaller than the length of the first conductive polymer film and the second porous member.

3. The flat stacked-type conductive polymer actuator according to claim 1, wherein
    at least a part of a peripheral portion of the porous member contains a curing agent.

4. A collective flat stacked-type conductive polymer actuator comprising a plurality of flat stacked-type conductive polymer actuators according to claim 1, wherein
    the first porous member and the second porous member of the adjacent actuators are connected with each other by using a link member.

5. A flat stacked-type conductive polymer actuator comprising:
    an electrolyte retention layer;
    a first conductive polymer film and a second conductive polymer film, having first end portions thereof being disposed to face each other and second end portions thereof being disposed to face each other, with the electrolyte retention layer being interposed therebetween;
    a first fixing member that has a first end portion to be secured to an outer surface of the first end portion of the first conductive polymer film and a second end portion to be secured to an outer surface of the second end portion of the second conductive polymer film; and
    a second fixing member that has a first end portion to be secured to an outer surface of the first end portion of the second conductive polymer film and a second end portion to be secured to an outer surface of the second end portion of the first conductive polymer film, wherein
    by applying an electric potential difference between the first conductive polymer film and the second conductive polymer film, one of the first conductive polymer film and the second conductive polymer film is expanded or contracted and the other conductive polymer film is contracted or expanded by an oxidation-reduction reaction, so that a driving force is externally outputted by displacements of the first fixing member and the second fixing member.

6. The flat stacked-type conductive polymer actuator according to claim 5, wherein
    the first conductive polymer film and the second conductive polymer film have a same length.

7. A collective flat stacked-type conductive polymer actuator comprising a plurality of flat stacked-type conductive polymer actuators, each according to claim 5, wherein
    in each of the actuators, by an oxidation-reduction reaction caused by applying an electric potential difference between the conductive polymer films that are connected to each other with the electrolyte retention layer interposed therebetween, one of the adjacent conductive polymer films is expanded or contracted and the other conductive polymer film is contracted or expanded, an adhesive agent is provided to connect the second fixing member of one of at least two adjacent flat conductive polymer actuators to the first fixing member of the other actuator, and by connecting the actuators with the adhesive agent, the displacements are added and increased.

* * * * *